United States Patent
Dinh et al.

(10) Patent No.: US 8,771,712 B2
(45) Date of Patent: Jul. 8, 2014

(54) TOPICAL ADMINISTRATION OF ACYCLOVIR

(75) Inventors: Steven Dinh, Briarcliff Manor, NY (US); Puchun Liu, Chappaqua, NY (US); Ihor Shevchuk, Yonkers, NY (US)

(73) Assignee: Emisphere Technologies, Inc., Roseland, NJ (US)

( * ) Notice: Subject to any disclaimer, the term of this patent is extended or adjusted under 35 U.S.C. 154(b) by 743 days.

(21) Appl. No.: 12/300,090

(22) PCT Filed: May 2, 2007

(86) PCT No.: PCT/US2007/067996
§ 371 (c)(1),
(2), (4) Date: Nov. 7, 2008

(87) PCT Pub. No.: WO2007/133944
PCT Pub. Date: Nov. 22, 2007

(65) Prior Publication Data
US 2009/0118168 A1 May 7, 2009

Related U.S. Application Data

(60) Provisional application No. 60/799,294, filed on May 9, 2006.

(51) Int. Cl.
*A61K 9/00* (2006.01)
*A61K 31/522* (2006.01)

(52) U.S. Cl.
USPC ..................................... 424/400; 514/263.37

(58) Field of Classification Search
USPC ..................................... 424/400; 514/263.37
See application file for complete search history.

(56) References Cited

U.S. PATENT DOCUMENTS

| | | | |
|---|---|---|---|
| 4,474,753 A | 10/1984 | Haslam et al. | |
| 4,963,555 A * | 10/1990 | Jones et al. | 514/263.38 |
| 5,002,932 A * | 3/1991 | Langelier et al. | 514/3.7 |
| 5,541,155 A | 7/1996 | Leone-Bay et al. | |
| 5,643,957 A | 7/1997 | Leone-Bay et al. | |
| 5,650,386 A * | 7/1997 | Leone-Bay et al. | 424/85.2 |
| 5,693,338 A | 12/1997 | Milstein | |
| 5,776,888 A | 7/1998 | Leone-Bay et al. | |
| 5,820,881 A | 10/1998 | Milstein | |
| 5,866,536 A | 2/1999 | Leone-Bay et al. | |
| 5,883,103 A * | 3/1999 | Burnside et al. | 514/263.38 |
| 5,955,503 A | 9/1999 | Leone-Bay et al. | |
| 5,965,121 A | 10/1999 | Leone-Bay et al. | |
| 5,976,569 A | 11/1999 | Milstein | |
| 5,989,539 A | 11/1999 | Leone-Bay et al. | |
| 6,001,347 A | 12/1999 | Leone-Bay et al. | |
| 6,071,510 A | 6/2000 | Leone-Bay et al. | |
| 6,100,298 A | 8/2000 | Leone-Bay et al. | |

(Continued)

FOREIGN PATENT DOCUMENTS

| WO | WO-9630036 A1 | 10/1996 |
|---|---|---|
| WO | WO-9834632 A1 | 8/1998 |

(Continued)

*Primary Examiner* — Shengjun Wang
(74) *Attorney, Agent, or Firm* — Blank Rome LLP

(57) ABSTRACT

The present invention provides a topical composition comprising (a) at least one delivery agent compound and (b) a acyclovir compound. Methods of treatment, and methods of preparing the topical composition are also provided.

7 Claims, 15 Drawing Sheets

Thickness (microns)
Stratum corneum
10-40
Viable epidermis
50-100
Dermis
300-500

Cross section view of skin layers

(56) References Cited

U.S. PATENT DOCUMENTS

| | | |
|---|---|---|
| 6,180,140 B1 | 1/2001 | Leone-Bay et al. |
| 6,221,367 B1 | 4/2001 | Milstein et al. |
| 6,242,495 B1 | 6/2001 | Leone-Bay et al. |
| 6,245,359 B1 | 6/2001 | Milstein et al. |
| 6,313,088 B1 | 11/2001 | Leone-Bay et al. |
| 6,331,318 B1 | 12/2001 | Milstein |
| 6,344,213 B1 | 2/2002 | Leone-Bay et al. |
| 6,346,242 B1 | 2/2002 | Leone-Bay et al. |
| 6,358,504 B1 | 3/2002 | Leone-Bay et al. |
| 6,375,983 B1 | 4/2002 | Kantor et al. |
| 6,384,278 B1 | 5/2002 | Tang et al. |
| 6,391,303 B1 | 5/2002 | Haas et al. |
| 6,395,774 B1 | 5/2002 | Milstein |
| 6,399,798 B2 | 6/2002 | Gschneidner et al. |
| 6,413,550 B1 | 7/2002 | Milstein et al. |
| 6,428,780 B2 | 8/2002 | Leone-Bay et al. |
| 6,440,929 B1 | 8/2002 | Milstein et al. |
| 6,461,545 B1 | 10/2002 | Kantor |
| 6,461,643 B2 | 10/2002 | Milstein et al. |
| 6,525,020 B2 | 2/2003 | Leone-Bay et al. |
| 6,558,706 B2 | 5/2003 | Kantor et al. |
| 6,610,329 B2 | 8/2003 | Santiago et al. |
| 6,623,731 B2 | 9/2003 | Leone-Bay et al. |
| 6,627,228 B1 | 9/2003 | Milstein et al. |
| 6,642,411 B1 | 11/2003 | Leone-Bay et al. |
| 6,646,162 B2 | 11/2003 | Tang et al. |
| 6,663,887 B2 | 12/2003 | Leone-Bay et al. |
| 6,663,898 B2 | 12/2003 | Milstein |
| 6,693,073 B2 | 2/2004 | Milstein et al. |
| 6,693,208 B2 | 2/2004 | Gscheidner et al. |
| 6,699,467 B2 | 3/2004 | Leone-Bay et al. |
| 6,846,844 B2 | 1/2005 | Tang |
| 2001/0003001 A1 | 6/2001 | Leone-Bay et al. |
| 2001/0039258 A1 | 11/2001 | Milstein et al. |
| 2002/0001591 A1 | 1/2002 | Santiago et al. |
| 2002/0013497 A1 | 1/2002 | Gschneidner et al. |
| 2002/0028250 A1 | 3/2002 | Milstein |
| 2002/0040061 A1 | 4/2002 | Tang et al. |
| 2002/0052422 A1 | 5/2002 | Milstein et al. |
| 2002/0065255 A1 | 5/2002 | Bay et al. |
| 2002/0102286 A1 | 8/2002 | Kantor et al. |
| 2002/0119910 A1 | 8/2002 | Leone-Bay et al. |
| 2002/0120009 A1 | 8/2002 | Leone-Bay et al. |
| 2002/0127202 A1 | 9/2002 | Leone-Bay et al. |
| 2002/0155993 A1 | 10/2002 | Milstein |
| 2003/0008900 A1 | 1/2003 | Leone-Bay et al. |
| 2003/0012817 A1 | 1/2003 | Milstein et al. |
| 2003/0045579 A1 | 3/2003 | Leone-Bay et al. |
| 2003/0072740 A1 | 4/2003 | Milstein et al. |
| 2003/0078302 A1 | 4/2003 | Leone-Bay et al. |
| 2003/0133953 A1 | 7/2003 | Milstein et al. |
| 2003/0171344 A1* | 9/2003 | Lekare ........................ 514/171 |
| 2003/0198658 A1 | 10/2003 | Milstein |
| 2003/0198666 A1 | 10/2003 | Abbas et al. |
| 2003/0225300 A1 | 12/2003 | Leone-Bay et al. |
| 2003/0232085 A1 | 12/2003 | Milstein et al. |
| 2003/0235612 A1 | 12/2003 | Leone-Bay et al. |
| 2004/0022856 A1 | 2/2004 | Sarubbi et al. |
| 2004/0062773 A1 | 4/2004 | Santiago et al. |
| 2004/0068013 A1 | 4/2004 | Leone-Bay et al. |
| 2004/0106825 A1 | 6/2004 | Bay et al. |
| 2004/0110839 A1 | 6/2004 | Leone-Bay et al. |
| 2005/0009748 A1 | 1/2005 | Dinh et al. |
| 2006/0084646 A1 | 4/2006 | Bernadino et al. |

FOREIGN PATENT DOCUMENTS

| | | |
|---|---|---|
| WO | WO 9912545 A2 * | 3/1999 |
| WO | WO-0007979 A2 | 2/2000 |
| WO | WO-0040203 A2 | 7/2000 |
| WO | WO-0047188 A1 | 8/2000 |
| WO | WO-0050386 A1 | 8/2000 |
| WO | WO-0059863 A1 | 10/2000 |
| WO | WO-0132130 A2 | 5/2001 |
| WO | WO-0132596 A1 | 5/2001 |
| WO | WO-0134114 A1 | 5/2001 |
| WO | WO-0144199 A1 | 6/2001 |
| WO | WO-0151454 A1 | 7/2001 |
| WO | WO-0170219 A1 | 9/2001 |
| WO | WO-0192206 A1 | 12/2001 |
| WO | WO-0202509 A1 | 1/2002 |
| WO | WO-0215959 A2 | 2/2002 |
| WO | WO-0216309 A1 | 2/2002 |
| WO | WO-0219969 A2 | 3/2002 |
| WO | WO-0220466 A1 | 3/2002 |
| WO | WO-02069937 A1 | 9/2002 |
| WO | WO-02070438 A2 | 9/2002 |
| WO | WO-02100338 A2 | 12/2002 |
| WO | WO-03026582 A2 | 4/2003 |
| WO | WO-03045306 A2 | 6/2003 |
| WO | WO-03045331 A2 | 6/2003 |
| WO | WO-03057170 A2 | 7/2003 |
| WO | WO-03057650 A2 | 7/2003 |
| WO | WO 2004024126 A1 * | 3/2004 |
| WO | WO-2004062587 A2 | 7/2004 |
| WO | WO-2004080401 A2 | 9/2004 |
| WO | WO-2004104018 A2 | 12/2004 |
| WO | WO-2005020925 A2 | 3/2005 |
| WO | WO-2005112633 A2 | 12/2005 |
| WO | WO 2005112937 A1 * | 12/2005 |
| WO | WO-2005117854 A2 | 12/2005 |

* cited by examiner

Cross section view of skin layers

Acyclovir skin permeation results skin

Acyclovir skin permeation results skin, Liomont Cicloferon

Acyclovir skin permeation results skin SNAC

Acyclovir Eth/wat/SNAC skin permeation results

Acyclovir Eth/wat skin permeation results

Acyclovir Eth/wat w/IPM skin permeation results

Acyclovir Eth/wat w/IPM w/SNAC skin permeation results

Acyclovir Eth/wat w/IPM skin permeation results

Acyclovir flux enhancement factor 11.7
Epidermal content enhancement factor 0.64
Dermal content enhancement factor 0.02

Cicloferon/Eth/SNAC skin permeation results

Acyclovir flux enhancement factor 16.6
Epidermal content enhancement factor 1.7
Dermal content enhancement factor 0.8

Cicloferon/Eth/IPM/SNAC skin permeation results

³H Acyclovir skin permeation results on skin

Acyclovir flux enhancement factor 3.1
Epidermal content enhancement factor 1.8

$^3$H Acyclovir cumulative skin permeation results on skin $^3$H Acyclovir skin permeation results on skin ³H Acyclovir cumulative skin permeation results on skin

TOPICAL ADMINISTRATION OF ACYCLOVIR

CROSS-REFERENCE TO PRIOR APPLICATIONS

This is a Non Provisional U.S. Application of a International Application and a Provisional application, claiming the benefit of PCT/US2007/067996 filed May 2, 2007; and U.S. Provisional Application No. 60/799,294 filed May 9, 2006.

FIELD OF THE INVENTION

The present invention relates to topical formulations containing acyclovir or a salt or analog thereof, such as acyclovir sodium, and a delivery agent compound.

BACKGROUND OF THE INVENTION

Skin conditions, such as herpes infections, are a widespread medical problem, with an increasing rate of prevalence. It has been reported that topically administered acyclovir, can be included in an effective protocol for the treatment of herpes infections. The topical application of acyclovir (2-amino-1,9-dihydro-9-[(2-hydroxyethoxy)methyl]-6H-purin-6-one) has multiple purposes including the treatment or prevention of mucocutaneous infections such as oral labial ("fever blisters"), gingivostomatitis; and ophthalmically for keratoconjuntivitis and recurrent epithelia keratitis.

For optimal performance a topical acyclovir product should maximize the acyclovir concentration delivered to the layer of the skin where the virus resides. It is believed that in oral labial infection the virus resides in melanocytes at the epidermal-dermal junction. These cells lie 60-140 μm beneath the skin surface. In-vivo measurement in humans of acyclovir transport into the dermis has been performed using Zovirax® and microdialysis for monitoring delivered acyclovir (Br. J Dermatol. 2003 March; 148(3):434-43; The role of stratum corneum and dermal microvascular perfusion in penetration and tissue levels of water-soluble drugs investigated by microdialysis; Morgan C J, Renwick A G, Friedmann P S). The $IC_{50}$ of Zovirax® cream (5%) against herpes simplex virus-1 isolates ranges from 0.02-13.5 mcg/mL and 0.01-9.9 mcg/mL for herpes simplex virus-2. (2006 Physicians Desk Reference entry for Zovirax cream.) In the study performed by Morgan et al., no acyclovir was detected in the dermis after application of acyclovir to intact skin. An acyclovir concentration of 3.9 μg/ml was achieved only after removal of the stratum corneum and reduction of cutaneous circulation by infusion of 0.0005% noradrenaline. (See Morgan, C J, ibid). Neither approach is suitable for a commercial product, but demonstrates the role of the stratum corneum as the main barrier to acyclovir transport, and the rapid clearance of acyclovir from the dermis due to cutaneous circulation.

There is a need for a composition which provides concentrations of acyclovir at the epidermal/dermal junction and would therefore increase its therapeutic benefits in the treatment of herpes simplex virus infection, including type 1 and type 2 herpes simplex viruses. Providing higher levels of acyclovir to the epidermal/dermal junction via topical administration may also increase indications for topical therapy.

SUMMARY OF THE INVENTION

The present invention is a topical composition comprising (a) at least one delivery agent compound, (b) an acyclovir component (e.g., acyclovir, valacyclovir and nucleoside antiviral analogs thereof and pharmaceutically acceptable salts thereof and (c) a vehicle for topical delivery. In one embodiment of the invention, the composition includes an effective amount of the acyclovir component and a delivery agent compound to treat or prevent the onset of a skin condition, particularly a skin condition caused or aggravated by herpes simplex virus types 1 and 2 (HSV-1 and HSV-2).

The delivery agent compound improves the delivery of the acyclovir component to the epidermal/dermal junction, where the HSV virus resides. For instance, the topical composition including a delivery agent compound can yield higher epidermis-layer concentrations of the acyclovir component over a period of time (e.g. 3 hours, 6 hours, 12 hours or 24 hours) after a single administration than a similar topical composition without the delivery agent compound.

The vehicle for topical delivery is a physiologically acceptable vehicle that facilitates application of the acyclovir component and delivery agent compound to the skin. For example, vehicle for topical delivery can be semi-aqueous and oil-based solution or suspension. Suitable vehicles for topical delivery include, but are not limited to, isopropylmyristate (IPM), and polyethylene glycol (PEG) and water solutions containing a thickening agent. The vehicle for topical delivery may be, for example, in the form of a cream, a gel, a lotion, an ointment, a suspension, an emulsion (e.g. an oil-in-water emulsion), depot delivery device and formulation as disclosed in U.S. Pat. Nos. 7,018,649, 5,240,711, 5,225,199, 5,879,701, 6,894,078, 6,998,138, 6,846,837, 6,620,435, and 6,586,473 which are hereby incorporated by reference in their entirety.

Another embodiment is a method for administering an acyclovir compound (e.g. Cicloferen® by LIOMONT Laboratories, S.A. de C.V.), an analogue thereof, or a mixture thereof to an animal (e.g., a patient) in need thereof, by topically administering the composition or dosage unit form(s) of the present invention to the animal.

Another embodiment is a method for administering a acyclovir compound (e.g. acyclovir), an analogue thereof, or a mixture thereof in combination with a topical analgesic (e.g., lidocaine, pramocaine, benzocaine, pramoxine, or mixtures thereof) to an animal (e.g., a patient) in need thereof, by topically administering the composition or dosage unit form(s) of the present invention to the animal.

Another embodiment is a method for administering a acyclovir compound (e.g. acyclovir), an analogue thereof, or a mixture thereof in combination with an antibiotic (e.g., aminoglycosides, cephalosporins, beta-lactams, chloramphenicol, glycopeptides, macrolides, penicillins, quinolones, sulfonamides, tetracylines, bacitracins, lincomycins, oxazolidinones, polymixins, rifamycins, streptogramins). Preferred antibiotics include neomycin, polymyxin B, gentamycin, amicacin, tobramycin, or mixtures thereof) to an animal (e.g., a patient) in need thereof, by topically administering the composition or dosage unit form(s) of the present invention to the animal.

Yet another embodiment is a method of treating skin conditions, including but not limited to herpes infections of the skin, mucous membranes or eyes in an animal in need thereof (e.g., a patient) by administering an effective amount of the composition or dosage unit form(s) of the present invention to the animal.

Yet another embodiment is a method of preparing a topical composition comprising mixing (a) at least one delivery agent compound, (b) at least one the acyclovir compound, and (c) a vehicle for topical delivery.

Yet another embodiment provides topical acyclovir compositions with a delivery agent compound that achieves dermal acyclovir concentrations in the $IC_{50}$ range, i.e., dermal acyclovir concentrations of at least about 0.01 mcg/mL, or at least about 0.02 mcg/mL, or at least about 0.1 mcg/mL, or at least about 1.0 mcg/mL, or at least about 2.0 mcg/mL, or at least about 3.0 mcg/mL, or at least about 4.0 mcg/mL, or at least about 5.0 mcg/mL, or at least about 6.0 mcg/mL, or at least about 7.0 mcg/mL, or at least about 8.0 mcg/mL, or at least about 9.0 mcg/mL, or at least about 10.0 mcg/mL, or at least about 11.0 mcg/mL, or at least about 12.0 mcg/mL, or at least about 13.0 mcg/mL.

Yet another embodiment of the present invention provides an acylovir topical formulation that has an acylovir component epidermal flux enhancement factor of at least 1.1, or at least 4, or at least 8, or at least 10, or at least 20, or least 40, or at least 80.

Yet another embodiment of the present invention is a topical composition prepared from a base formulation comprising the commercial topical acyclovir product Cicloferon®, available from Liomont S.K. de C.V (Colonia Centro Cuajimalpa, Mexico).

Yet another embodiment is a composition of the present invention comprising acyclovir and one or more delivery agent compounds in which the addition of the delivery agent compound provides an acyclovir influx into the dermis at a rat of about 0.01 mcg/cm$^2$-hr to about 15.8 mcg/cm$^2$-hr.

Yet another embodiment is a composition of the present invention comprising acyclovir and one or more delivery agent compound in which provides continuous influx of acyclovir through the epidermis for a period of time (e.g., 3 hours, 6 hours, 12 hours, 24 hours or 36 hours).

Yet another embodiment is a topical acyclovir composition (e.g., Cicloferon®) further comprising SNAC and/or an alcohol.

Yet another embodiment is a composition of the present invention comprising Cicloferon and SNAC and an alcohol (e.g. ethanol).

Yet another embodiment is a composition of the present invention comprising Cicloferon and about 4% SNAC plus Ethanol and water in a ratio of about 1:1.

Yet another embodiment is a composition of the present invention comprising Cicloferon and SNAC plus Ethanol and IPM.

Yet another embodiment is a composition of the present invention comprising Cicloferon and about 4% SNAC plus about up to 40% Ethanol and about 3% water and about up to 30% IPM.

DETAILED DESCRIPTION OF THE INVENTION

Definitions

Figure 1:
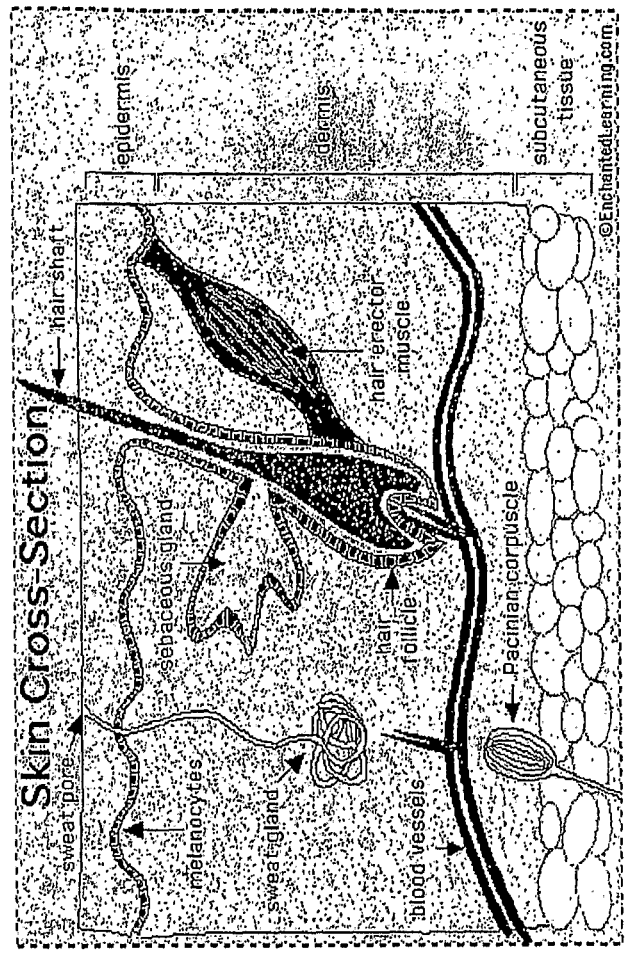
FIG. 1 is cross section of skin layers.
Figure 1:
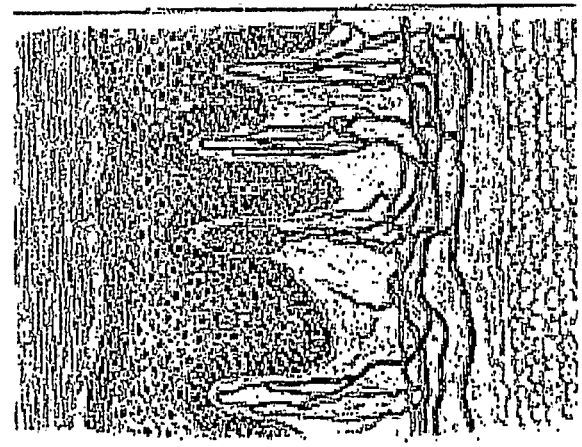

The term "hydrate" as used herein includes, but is not limited to, (i) a substance containing water combined in the molecular form and (ii) a crystalline substance containing one or more molecules of water of crystallization or a crystalline material containing free water.

The term "solvate" as used herein includes, but is not limited to, a molecular or ionic complex of molecules or ions of a solvent with molecules or ions of the delivery agent compound or salt thereof, or hydrate or solvate thereof.

The term "delivery agent" refers to any of the delivery agent compounds disclosed herein.

The term "SNAC" refers to the monosodium salt of N-(8-[2-hydroxybenzoyl]-amino)caprylic acid.

The term "SNAD" refers to the monosodium salt of N-(10-[2-hydroxybenzoyl]-amino)decanoic acid. The term "disodium salt of SNAD" refers to the disodium salt of N-(10-[2-hydroxybenzoyl]-amino)decanoic acid.

An "effective amount of the acyclovir component" is an amount of the acyclovir component which is effective to treat or prevent the condition for which it is administered in a living organism over some period of time, e.g., an amount which provides a therapeutic effect. Indications for which a acyclovir compound is administered are known to those skilled in the art, some of which are disclosed herein, and also include those conditions that can be treated or prevented with a acyclovir compound which are to be later discovered.

An "effective amount of delivery agent" is an amount of the delivery agent which enables and/or facilitates an increased concentration of the acyclovir component in the epidermis layer of the skin, as compared the concentration of the acyclovir component in the epidermis upon administration of the acyclovir component without the delivery agent.

The term "mean", when preceding a pharmacokinetic value (e.g., mean peak) represents the arithmetic mean value of the pharmacokinetic value unless otherwise specified.

The term "acylovir component epidermal flux enhancement factor" refers to the ratio of (a):(b), wherein (a) is the acyclovir component (e.g. acyclovir or valacyclovir) flux through the epidermis for a composition containing an additive to increase flux (e.g. a delivery agent compound or an alcohol) and (b) is the acyclovir component flux through the epidermis for the otherwise same composition that does not contain the additive to increase flux.

As used herein and in the appended claims, the singular forms "a," "an," and "the," include plural referents unless the context clearly indicates otherwise. Thus, for example, reference to "a molecule" includes one or more of such molecules, "a reagent" includes one or more of such different reagents, reference to "an antibody" includes one or more of such different antibodies, and reference to "the method" includes reference to equivalent steps and methods known to those of ordinary skill in the art that could be modified or substituted for the methods described herein.

The term "about" generally means within 10%, preferably within 5%, and more preferably within 1% of a given value or range.

The terms "alkyl" and "alkenyl" as used herein include linear and branched alkyl and alkenyl substituents, respectively.

The term "patient" as used herein refers to a mammal and preferably a human.

The phrase "pharmaceutically acceptable" refers to additives or compositions that are physiologically tolerable and do not typically produce an allergic or similar untoward reaction, such as rash, welts, swelling, increased sensitivity, and the like, when administered to the skin or mucous membranes of a patient.

Acyclovir Component

The term "acyclovir" refers to 9-(2-hydroxyethoxymethyl) guanine. Suitable salts (e.g., pharmaceutically acceptable salts) and esters of acyclovir are described in U.S. Pat. No. 4,199,574, which is hereby incorporated by reference, and include, but are not limited to, sodium acyclovir and acyclovir valerate. Acyclovir also forms acid addition salts; such as with hydrochloric, sulphuric, phosphoric, maleic, fumaric, citric, tartaric, lactic and acetic acid.

A synthesis of acyclovir is disclosed in U.S. Pat. No. 4,199, 574, which is hereby incorporated by reference. Acyclovir is commercially available from GlaxoSmithKline (Research Triangle Park, N.C.) under the tradename Zovirax®.

Any prodrug which is converted in vivo to 9-(2-hydroxyethoxymethyl) guanine can also be used. As used herein, the term "acyclovir" or "acyclovir component" includes prodrugs of acyclovir. The term "prodrug" as used herein includes pharmaceutically acceptable salts of the drug. Acyclovir prodrugs include, substituted purines of the formula:

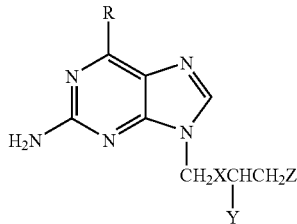

or salts thereof, wherein:
R is hydrogen, hydroxy, or amino;
X is oxygen or sulphur;
Y is hydrogen or hydroxymethyl; and
Z is —H, $C_{1-16}$ alkyl, or —OCOCH($R_1$)$NH_2$, wherein $R_1$ is —CH[$CH_3$]$_2$.

Suitable acyclovir prodrugs, include but are not limited to, those described in U.S. Pat. Nos. 4,609,662, 4,758,572 and 4,957,924, all of which are hereby incorporated by reference. A non-limiting example of such a prodrug is 2-[(2-amino-1, 6-dihydro-6-oxo-9H-purin-9-yl)methoxy]ethyl ester (valacyclovir) and its pharmaceutically acceptable salts (e.g. valacyclovir hydrochloride). Valacyclovir is commercially available as its hydrochloride salt from GlaxoSmithKline (Research Triangle Park, N.C.) under the tradename Valtrex™.

Therapeutically effective amounts of a acyclovir for use in treatment of all conditions and disorders described herein, is an amount sufficient to suppress or alleviate conditions associated with the viral infection. As will be recognized by those in the field, an effective amount of therapeutic agent will vary with many factors including the potency of the acyclovir or salt, ester, or prodrug thereof, the age and weight of the patient, and the severity of the condition or disorder to be treated.

According to one embodiment, the compositions of the present invention contain from about 0.5% to about 20% by weight of an acyclovir component. According to another embodiment, the composition contains from about 1% to about 10% by weight, or from about 3% to about 6%, or from about 4% to about 5% by weight of an acylovir component.

The acyclovir and delivery agent compound may be administered separately or together with one or more other active agents. For example, the acyclovir and delivery agent compound may be administered separately or together with compounds or compositions that exhibit antiviral activity, such as compounds used to treat retroviral infections (particularly HIV infections), e.g., 3'-azido-3'-deoxythymidine (AZT) and/or compounds or compositions that exhibit activity as ribonucleotide reductase inhibitors. Suitable ribonucleotide reductase inhibitors include, but are not limited to, thiocarbonohydrazone ribonucleotide reductase inhibitors, such as those disclosed in U.S. Pat. No. 5,393,883, which is hereby incorporated by reference. Additional antiviral agents that may be included in the compositions of the present invention include docosanol, penciclovi, fomivirsen and trifluridine.

Delivery Agent Compounds

In one embodiment of the present invention, the delivery agent compound has the following structure, or a pharmaceutically acceptable salt thereof:

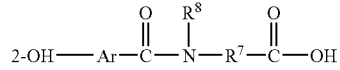

Formula A wherein
Ar is phenyl or naphthyl;
Ar is optionally substituted with one or more of —OH, halogen, $C_1$-$C_4$ alkyl, $C_1$-$C_4$ alkenyl, $C_1$-$C_4$ alkoxy or $C_1$-$C_4$ haloalkoxy;

$R^7$ is $C_4$-$C_{20}$ alkyl, $C_4$-$C_{20}$ alkenyl, phenyl, naphthyl, ($C_1$-$C_{10}$ alkyl) phenyl, ($C_1$-$C_{10}$ alkenyl)phenyl, ($C_1$-$C_{10}$ alkyl) naphthyl, ($C_1$-$C_{10}$ alkenyl) naphthyl, phenyl($C_1$-$C_{10}$ alkyl), phenyl($C_1$-$C_{10}$ alkenyl), naphthyl($C_1$-$C_{10}$ alkyl), or naphthyl ($C_1$-$C_{10}$ alkenyl);

$R^8$ is hydrogen, $C_1$ to $C_4$ alkyl, $C_2$ to $C_4$ alkenyl, $C_1$ to $C_4$ alkoxy, or $C_1$-$C_4$ haloalkoxy;

$R^7$ is optionally substituted with $C_1$ to $C_4$ alkyl, $C_2$ to $C_4$ alkenyl, $C_1$ to $C_4$ alkoxy, $C_1$-$C_4$ haloalkoxy, —OH, —SH, —$CO_2R^9$, or any combination thereof;

$R^9$ is hydrogen, $C_1$ to $C_4$ alkyl, or $C_2$ to $C_4$ alkenyl; and $R^7$ is optionally interrupted by oxygen, nitrogen, sulfur or any combination thereof.

In one embodiment, the delivery agent compounds are not substituted with an amino group in the position alpha to the acid group.

Suitable delivery agent compounds include, but are not limited to, N-(8-[2-hydroxybenzoyl]-amino)caprylic acid and salts thereof, e.g., a sodium salt of N-(8-[2-hydroxybenzoyl]-amino)caprylic acid, such as a mono- or di-sodium salt, N-(8-[2-hydroxybenzoyl]-amino) decanoic acid and pharmaceutically acceptable salts thereof, including its monosodium salt, 4-[(4-chloro-2-hydroxy-benzoyl)amino]butanoic acid (also known as 4-[(2-hydroxy-4-chlorobenzoyl)amino]butanoate) and pharmaceutically acceptable salts thereof, including its sodium salt (e.g., monosodium salt), N-(8-[2-hydroxy-5-chlorobenzoyl]-amino)octanoic acid (also known as 8-(N-2-hydroxy-5-chlorobenzoyl)aminocaprylic acid)) and pharmaceutically acceptable salts thereof, including its monosodium salt, and 8-(N-2-hydroxy-4-methoxybenzoyl)-aminocaprylic acid and pharmaceutically acceptable salts thereof, including its monosodium salt.

According to one embodiment, $R^7$ in Formula A is selected from $C_8$-$C_{20}$ alkyl, $C_8$-$C_{20}$ alkenyl, phenyl, naphthyl, ($C_1$-$C_{10}$ alkyl) phenyl, ($C_1$-$C_{10}$ alkenyl)phenyl, ($C_1$-$C_{10}$ alkyl) naphthyl, ($C_1$-$C_{10}$ alkenyl) naphthyl, phenyl($C_1$-$C_{10}$ alkyl), phenyl ($C_1$-$C_{10}$ alkenyl), naphthyl($C_1$-$C_{10}$ alkyl), and naphthyl($C_1$-$C_{10}$ alkenyl).

According to another embodiment, $R^7$ in Formula A is selected from $C_8$-$C_{20}$ alkyl, and $C_8$-$C_{20}$ alkenyl.

In another embodiment of the present invention, the delivery agent compound has the following structure, or a pharmaceutically acceptable salt thereof:

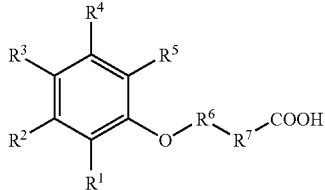

Formula B wherein $R^1$, $R^2$, $R^3$, and $R^4$ are independently H, —OH, halogen, $C_1$-$C_4$ alkyl, $C_2$-$C_4$ alkenyl, $C_1$-$C_4$ alkoxy, —C(O)$R^8$, —NO$_2$, —NR$^9$R$^{10}$, or —N$^+$R$^9$R$^{10}$R$^{11}$(R$^{12}$);

$R^5$ is H, —OH, —NO$_2$, halogen, —CF$_3$, —NR$^{14}$R$^{15}$, —N$^+$R$^{14}$R$^{15}$R$^{16}$(R$^{13}$)$^-$, amide, $C_1$-$C_{12}$ alkoxy, $C_1$-$C_{12}$ alkyl, $C_2$-$C_{12}$ alkenyl, carbamate, carbonate, urea, or —C(O)R$^{18}$;

$R^5$ is optionally substituted with halogen, —OH, —SH, or —COOH;

$R^5$ is optionally interrupted by O, N, S, or —C(O)—;

$R^6$ is a $C_1$-$C_{12}$ alkylene, $C_2$-$C_{12}$ alkenylene, or arylene;

$R^6$ is optionally substituted with a $C_1$-$C_4$ alkyl, $C_2$-$C_4$ alkenyl, $C_1$-$C_4$ alkoxy, —OH, —SH, halogen, —NH$_2$, or —CO$_2$R$^8$;

$R^6$ is optionally interrupted by O or N;

$R^7$ is a bond or arylene;

$R^7$ is optionally substituted with —OH, halogen, —C(O)CH$_3$, —NR$^{10}$R$^{11}$, or —N$^+$R$^{10}$R$^{11}$R$^{12}$(R$^{13}$)$^-$;

each occurrence of $R^8$ is independently H, $C_1$-$C_4$ alkyl, $C_2$-$C_4$ alkenyl, or —NH$_2$;

$R^9$, $R^{10}$, $R^{11}$, and $R^{12}$ independently H or $C_1$-$C_{10}$ alkyl;

$R^{13}$ is a halide, hydroxide, sulfate, tetrafluoroborate, or phosphate;

$R^{14}$, $R^{15}$ and $R^{16}$ are independently H, $C_1$-$C_{10}$ alkyl, $C_1$-$C_{10}$ alkyl substituted with —COOH, $C_2$-$C_{12}$ alkenyl, $C_2$-$C_{12}$ alkenyl substituted with —COOH, or —C(O)R$^{17}$;

$R^{17}$ is —OH, $C_1$-$C_{10}$ alkyl, or $C_2$-$C_{12}$ alkenyl; and $R^{18}$ is H, $C_1$-$C_6$ alkyl, —OH, —NR$^{14}$R$^{15}$, or N$^+$R$^{14}$R$^{15}$R$^{16}$(R$^{13}$)$^-$.

In one particular embodiment, when $R^1$, $R^2$, $R^3$, $R^4$, and $R^5$ are H, and $R^7$ is a bond then $R^6$ is not a $C_1$-$C_6$, $C_9$ or $C_{10}$ alkyl.

In another embodiment, when $R^1$, $R^2$, $R^3$, and $R^4$ are H, $R^5$ is —OH, and $R^7$ is a bond then $R^6$ is not a $C_1$-$C_3$ alkyl.

In yet another embodiment, when at least one of $R^1$, $R^2$, $R^3$, and $R^4$ is not H, $R^5$ is —OH, and $R^7$ is a bond, then $R^6$ is not a $C_1$-$C_4$ alkyl.

In yet another embodiment, when $R^1$, $R^2$, and $R^3$ are H, $R^4$ is —OCH$_3$, $R^5$ is —C(O)CH$_3$, and $R^6$ is a bond then $R^7$ is not a $C_3$ alkyl.

In yet another embodiment, when $R^1$, $R^2$, $R^4$, and $R^5$ are H, $R^3$ is —OH, and $R^7$ is a bond then $R^6$ is not a methyl.

In yet another embodiment, $R^6$ of Formula B is a $C_8$-$C_{12}$ alkylene, $C_8$-$C_{12}$ alkenylene, or arylene.

In yet another embodiment of the present invention, the delivery agent compound has the following structure or a pharmaceutically acceptable salt thereof:

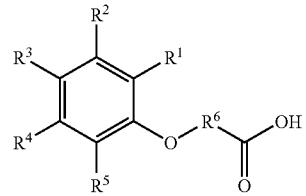

Formula C wherein $R^1$, $R^2$, $R^3$, $R^4$ and $R^5$ are independently H, —CN, —OH, —OCH$_3$, or halogen, at least one of $R^1$, $R^2$, $R^3$, $R^4$ and $R^5$ being —CN; and $R^6$ is a $C_1$-$C_{12}$ linear or branched alkylene, a $C_1$-$C_{12}$ linear or branched alkenylene, a $C_1$-$C_{12}$ linear or branched arylene, an alkyl(arylene) or an aryl(alkylene).

According to one embodiment, when $R^1$ is —CN, $R^4$ is H or —CN, and $R^2$, $R^3$, and $R^5$ are H, then $R^6$ is not methylene ((CH$_2$)$_1$).

In another embodiment, $R^6$ of Formula C is a $C_8$-$C_{12}$ linear or branched alkylene, a $C_8$-$C_{12}$ linear or branched alkenylene, an arylene, an alkyl(arylene) or an aryl(alkylene).

In yet another embodiment, $R^6$ of Formula C is a $C_8$-$C_{12}$ linear or branched alkylene, a $C_8$-$C_{12}$ linear or branched alkenylene Other suitable delivery agent compounds are disclosed in U.S. Pat. No. 6,627,228, which is hereby incorporated by reference.

In embodiments of the present invention, delivery agent compounds to be used in the topical composition along with the acyclovir compound include, but are not limited to, a polymeric delivery agent comprising a polymer conjugated to a modified amino acid or derivative thereof via a linkage group selected from the group consisting of —NHC(O)NH—, —C(O)NH—, —NHC(O)—, —OOC—, —COO—, —NHC(O)O—, —OC(O)NH—, —CH$_2$NH—, —NHCH$_2$—, —CH$_2$NHC(O)O—, —OC(O)NHCH$_2$—, —CH$_2$NHCOCH$_2$O—, —OCH$_2$C(O)NHCH$_2$—, —NHC(O)CH$_2$O—, —OCH$_2$C(O)NH—, —NH—, —O—, and carbon-carbon bond. In one embodiment, the polymeric delivery agent is not a polypeptide or polyamino acid. In another embodiment, the modified amino acid has the structure of formula A, B, or C. In one embodiment, the polymeric delivery agent includes a modified amino acid having the structure:

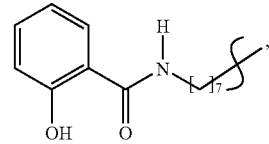

Formula D which is conjugated via a —COO group to a polymer having monomers derived from polyethylene glycol.

In one embodiment, the polymeric delivery agent is a modified amino acid having the structure of Formula D conjugated via a —COO group to a polymer having the structure:

—CH$_2$CH$_2$O(CH$_2$CH$_2$O)$_x$CH$_2$CH$_2$O—Y, wherein x is from 1-14; and

Y is H or CH$_3$.

According to one embodiment, the polymeric delivery agent is compound having the structure of Formula D conjugated via a —COO group to a polymer having the structure:

wherein x is 1-9; and

Y is $CH_3$ or H. For example, the polymeric delivery agent can be 8-(2-hydroxybenzoylamino)-octanoic acid 2-{2-[2-(2-{2-[2-(2-methoxyethoxy)ethoxy]ethoxy}-ethoxy)ethoxy]ethoxy}ethyl ester.

In one embodiment, the delivery agent compound is PEGylated SNAC with an average of about 6-9 or about 7-8 (e.g. 7.3) repeating ethylene oxide groups and having a molecular weight of about 500-800 (e.g. 600) daltons.

Delivery agent compounds of the present invention include compounds as shown below and pharmaceutically acceptable salts thereof:

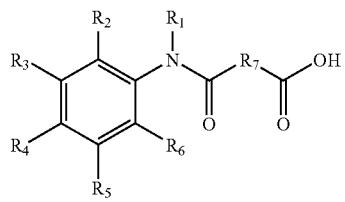

Formula E wherein:

$R_1$ is —$(CH_2)_m$—$R_8$, wherein m=0 or 1;

$R_2$-$R_6$ are independently selected from hydrogen, hydroxyl, halogen, $C_1$-$C_4$ alkyl, $C_2$-$C_4$ alkenyl, $C_2$-$C_4$ alkynyl, $C_1$-$C_4$ alkoxy, and cyano;

$R_7$ is selected from $C_1$-$C_{10}$ alkyl, $C_2$-$C_{10}$ alkenyl, and $C_2$-$C_{10}$ alkynyl;

$R_8$ is selected from cyclopentyl, cyclohexyl and phenyl, wherein when $R_8$ is a phenyl, m=1; and $R_8$ is optionally substituted with $C_1$-$C_4$ alkyl, $C_1$-$C_4$ alkoxy, halogen or hydroxyl, or a combination thereof.

Other delivery agent compounds of the present invention include those of the formula:

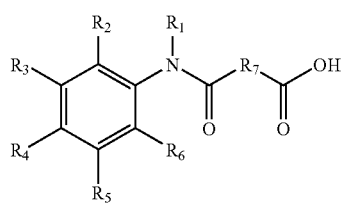

Formula F and pharmaceutically acceptable salts thereof, wherein:

$R_1$ is a $C_1$-$C_6$ alkyl, or $C_2$-$C_6$ alkenyl, $R_2$-$R_6$ are independently chosen from the group consisting of hydrogen, hydroxyl, halogen, $C_1$-$C_4$ alkyl, $C_2$-$C_4$ alkenyl, $C_2$-$C_4$ alkynyl, $C_1$-$C_4$ alkoxy, and cyano, and $R_7$ is selected from the group consisting of $C_1$-$C_{10}$ alkyl, $C_2$-$C_{10}$ alkenyl, and $C_2$-$C_{10}$ alkynyl.

Other delivery agent compounds of the present invention include those of the formula:

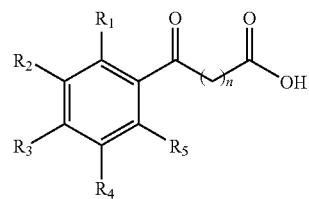

Formula G and pharmaceutically acceptable salts thereof, wherein n=1 to 9, and $R_1$ to $R_5$ are independently hydrogen, $C_1$ to $C_4$ alkyl, $C_1$ to $C_4$ alkoxy, $C_2$ to $C_4$ alkenyl, halogen, hydroxyl, —NH—C(O)—$CH_3$, or —O—$C_6H_5$.

Other delivery agent compounds of the present invention include those of the formula:

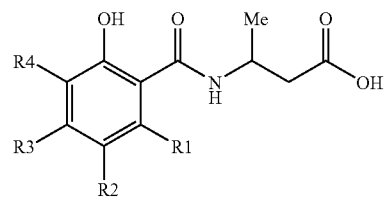

Formula H and pharmaceutically acceptable salts thereof, wherein $R_1$ to $R_4$ are independently hydrogen, $C_1$ to $C_4$ alkyl, $C_2$ to $C_4$ alkenyl, halogen, $C_1$ to $C_4$ alkoxy, or hydroxyl.

Other delivery agent compounds of the present invention include those of the formula:

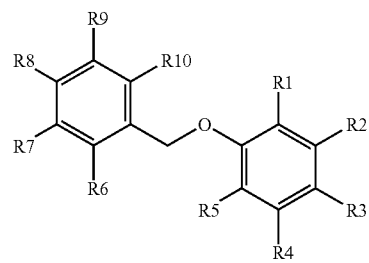

Formula I and pharmaceutically acceptable salts thereof, wherein one of R1 to R5 has the generic structure

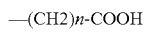

where n=0-6;

the remaining four members of $R_1$ to $R_5$ are independently hydrogen, $C_1$ to $C_4$ alkyl, $C_2$ to $C_4$ alkenyl, halogen, $C_1$ to $C_4$ alkoxy, or hydroxyl; and $R_6$-$R_{10}$ are independently hydrogen, $C_1$ to $C_4$ alkyl, $C_2$ to $C_4$ alkenyl, halogen, $C_1$ to $C_4$ alkoxy, or hydroxyl.

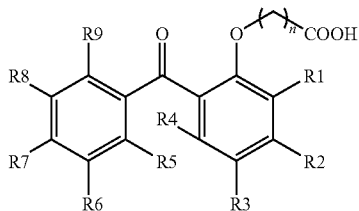

Formula J and pharmaceutically acceptable salts thereof, wherein
n=1 to 9; and
$R_1$ to $R_9$ are independently hydrogen, $C_1$ to $C_4$ alkyl, $C_2$ to $C_4$ alkenyl, halogen, $C_1$ to $C_4$ alkoxy, or hydroxyl.

Other delivery agent compounds of the present invention include those of the formula:

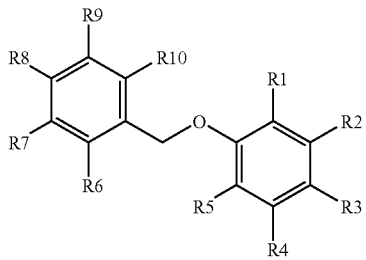

Formula K and pharmaceutically acceptable salts thereof, wherein
$R_1$-$R_5$ are independently hydrogen, $C_1$ to $C_4$ alkyl, $C_2$ to $C_4$ alkenyl, halogen, $C_1$ to $C_4$ alkoxy, hydroxyl, or —O—(CH2)n—COOH (where n is 1 to 12);
at least one of $R_1$ to $R_5$ has the generic structure

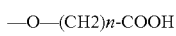

where n=1-12; and
$R_6$-$R_{10}$ are independently hydrogen, $C_1$ to $C_4$ alkyl, $C_2$ to $C_4$ alkenyl, halogen, $C_1$ to $C_4$ alkoxy, or hydroxyl. International Application Nos. PCT/US2005/017339 and PCT/US2005/017309, filed May 16, 2005 and their priority documents, U.S. Provisional Application No. 60/576,088, filed Jun. 1, 2004, U.S. Provisional Application No. 60/576,397, filed Jun. 1, 2004, U.S. Provisional Application No. 60/576,105, filed Jun. 1, 2004, U.S. Provisional Application No. 60/571,090, filed May 14, 2004, U.S. Provisional Application No. 60/571,092, filed May 14, 2004, U.S. Provisional Application No. 60/571,195, filed May 14, 2004, U.S. Provisional Application No. 60/571,194, filed May 14, 2004, U.S. Provisional Application No. 60/571,093, filed May 14, 2004, U.S. Provisional Application No. 60/571,055, filed May 14, 2004, U.S. Provisional Application No. 60/571,151, filed May 14, 2004, U.S. Provisional Application No. 60/571,315, filed May 14, 2004, U.S. Provisional Application No. 60/571,144, filed May 14, 2004, and U.S. Provisional Application 60/571,089, filed May 14, 2004, are hereby incorporated by reference in their entirety.

The delivery agent compound may be any of those described in U.S. Pat. Nos. 6,846,844, 6,699,467, 6,693,208, 6,693,208, 6,693,073, 6,663,898, 6,663,887, 6,646,162, 6,642,411, 6,627,228, 6,623,731, 6,610,329, 6,558,706, 6,525,020, 6,461,643, 6,461,545, 6,440,929, 6,428,780, 6,413,550, 6,399,798, 6,395,774, 6,391,303, 6,384,278, 6,375,983, 6,358,504, 6,346,242, 6,344,213, 6,331,318, 6,313,088, 6,245,359, 6,242,495, 6,221,367, 6,180,140, 5,541,155, 5,693,338, 5,976,569, 5,643,957, 5,955,503, 6,100,298, 5,650,386, 5,866,536, 5,965,121, 5,989,539, 6,001,347, 6,071,510, and 5,820,881; U.S. Published Application Nos. 20050009748, 20040110839, 20040106825, 20040068013, 20040062773, 20040022856, 20030235612, 20030232085, 20030225300, 20030198658, 20030133953, 20030078302, 20030072740, 20030045579, 20030012817, 20030008900, 20020155993, 20020127202, 20020120009, 20020119910, 20020102286, 20020065255, 20020052422, 20020040061, 20020028250, 20020013497, 20020001591, 20010039258, 20010003001 International Publication Nos. WO 2005/020925, WO 2004/104018, WO 2004/080401, WO 2004/062587, WO 2003/057650, WO 2003/057170, WO 2003/045331, WO 2003/045306, WO 2003/026582, WO 2002/100338, WO 2002/070438, WO 2002/069937, WO 02/20466, WO 02/19969, WO 02/16309, WO 02/15959, WO 02/02509, WO 01/92206, WO 01/70219, WO 01/51454, WO 01/44199, WO 01/34114, WO 01/32596, WO 01/32130, WO 00/07979, WO 00/59863, WO 00/50386, WO 00/47188, WO 00/40203, and WO 96/30036, all of which are hereby incorporated by reference in their entirety.

Non-limiting examples of delivery agent compounds include N-(8-[2-hydroxybenzoyl]-amino)caprylic acid, N-(10-[2-hydroxybenzoyl]-amino)decanoic acid, 8-(2-hydroxy-4-methoxybenzoylamino)octanoic acid, 4-[(2-hydroxy-4-chlorobenzoyl)amino]butanoate, 8-(2,6-dihydroxybenzoylamino)octanoic acid, 8-(2-hydroxy-5-bromobenzoylamino)octanoic acid, 8-(2-hydroxy-5-chlorobenzoylamino)octanoic acid, 8-(2-hydroxy-5-iodobenzoylamino)octanoic acid, 8-(2-hydroxy-5-methylbenzoylamino)octanoic acid, 8-(2-hydroxy-5-fluorobenzoylamino)octanoic acid, 8-(2-hydroxy-5-methoxybenzoylamino)octanoic acid, 8-(3-hydroxyphenoxy)octanoic acid, 8-(4-hydroxyphenoxy)octanoic acid, 6-(2-cyanophenoxy)hexanoic acid, 8-(2-Hydroxyphenoxy)octyl-diethanolamine, 8-(4-hydroxyphenoxy)octanoate, 8-(4-hydroxyphenoxy)octanoate, 8-(2-hydroxy-4-methoxybenzoylamino)octanoic acid, 8-(2-hydroxy-5-methoxybenzoylamino)-octanoic acid, and salts thereof. Preferred salts include, but are not limited to, monosodium and disodium salts.

The delivery agent compounds may be in the form of the carboxylic acid or pharmaceutically acceptable salts thereof, such as sodium salts, and hydrates and solvates thereof. The salts may be mono- or multivalent salts, such as monosodium salts and disodium salts. The delivery agent compounds may contain different counter ions chosen for example due to their effect on modifying the dissolution profile of the delivery agent compound.

The delivery agent compounds may be prepared by methods known in the art, such as those discussed in the aforementioned publications (e.g., International Publication Nos. WO 98/34632, WO 00/07979, WO 01/44199, WO 01/32596, WO 02/20466, and WO 03/045306). SNAC, SNAD, and the free acid and other salts thereof may be prepared by any method known in the art, such as those described in U.S. Pat. Nos. 5,650,386 and 5,866,536.

Salts of the delivery agent compounds of the present invention may be prepared by methods known in the art. For example, sodium salts may be prepared by dissolving the delivery agent compound in ethanol and adding aqueous sodium hydroxide.

The delivery agent compound may be purified by recrystallization or by fractionation on one or more solid chromatographic supports, alone or linked in tandem. Suitable recrystallization solvent systems include, but are not limited to, acetonitrile, methanol, and tetrahydrofuran. Fractionation may be performed on a suitable chromatographic support such as alumina, using methanol/n-propanol mixtures as the mobile phase; reverse phase chromatography using trifluoroacetic acid/acetonitrile mixtures as the mobile phase; and ion exchange chromatography using water or an appropriate buffer as the mobile phase. When anion exchange chromatography is performed, preferably a 0-500 mM sodium chloride gradient is employed.

In one embodiment, the weight ratio of delivery agent to acyclovir compound ranges from about 0.1:1 to about 2000:1. The weight ratio may vary according to the acyclovir compound delivered and the particular indication for which it is administered.

Vehicles for Topical Delivery

Embodiments of the present invention include a cream or ointment base as a vehicle for topical delivery. This is particularly true where the composition is used on dry or peeling skin and when a moisturizing vehicle may otherwise be desirable. Suitable bases include lanolin, SILVADENE™ (silver sulfadiazine) (Hoechst Marion Roussel, Kansas City, Mo.), particularly for treatment of burns, AQUAPHOR™ (Duke Laboratories, South Norwalk, Conn.), and like bases.

Viscosity building agents may also serve as vehicles for topical delivery, and can be added to aqueous or oil based solutions to form a cream or gel. Examples of viscosity building agents include such as polyethylene glycol, gelatin, chitosan and its derivatives, hydrophilic cellulose (preferably a hydroxyalkylcellulose and more preferably, hydroxymethylcellulose, hydroxyethylcellulose, hydroxypropylcellulose or the like or a mixture thereof), and polyacrylate-polyacrylic acid polymers (e.g., Carbomers and the like).

Other vehicles for topical delivery include, but are not limited to, urea-based emollients, petroleum-based ointments, paste, lotion, liquid paraffin, lanolin, beeswax, vegetable oil, glycerin monostearate, higher alcohols, oil-in-water emulsion, or a water-in-oil emulsion. Further examples of vehicles for topical delivery include those topical agents disclosed in U.S. Pat. Nos. 7,018,660 and 6,994,863, both of which are hereby incorporated by reference in their entirety.

Delivery Systems

The composition of the present invention comprises one or more delivery agent compounds of the present invention and/or one or more acyclovir compounds. The delivery agent compound and acyclovir compound are typically mixed prior to administration to form an administration composition (which may comprise a unit dosage form).

The administration composition of the present invention may also contain other active ingredients such as those discussed in International Publication No. 99/60997 which is hereby incorporated by reference, anti-allergic medications (e.g. oxatamide), glucocorticoids or corticosteroids (e.g. betamethasone valerate, dexamethasone, triamcinolone acetonide, clobetasone butyrate, hydrocortisone and triamcinolone).

The administration compositions of the present invention may also contain nonsteroidal anti-inflammatory agents, including, but not limited to, flurbiprofen and ketorolace.

The administration composition may also contain other active ingredients such as antibiotics, pain relievers and local anesthetics. Limiting example include lidocaine, benzocaine, articaine, chlorprocaine, cocaine, dydloninem, proparacaine, mepivacaine, prilocaine, procaine, tetracaine, and pramoxine.

The administration composition may also contain other ingredients known to provide therapeutic effects to skin. These ingredients include, but are not limited to, aloe, antioxidants, moisturizers or humectants, vitamins, surfactants, hydroxy acids, proteolytic enzymes, skin lightening agents (e.g. melanin inhibitors, melanin bleaches), sunscreen, colorants, perfumes, preservatives, pigments, antiseptic agents, and toners. Any of the ingredients listed in the *International Cosmetic Ingredient Dictionary and Handbook*, $9^{th}$ Ed. 2002, by The Cosmetic Toiletry Fragrance Association (ISBN 1882621298), which is hereby incorporated by reference in its entirety, may be incorporated into the administration composition of the present invention.

The administration composition is typically applied topically to a targeted area of skin. The administration composition may be applied daily, for typically at least several days. However, more frequent application is also contemplated. For example, in the treatment of injured tissue, such as a rash, or an allergy-induced skin problem, it may be desirable to continuously maintain the administration composition on the affected area during healing, with applications of the administration composition from two to four times a day or more frequently. Use may also be for extended periods, including years.

If desired, it is possible to incorporate either aqueous or water-oil base compositions in bandages or other wound dressings to provide for continuous exposure of the affected area to the topical composition. Aerosol applicators may also find use.

The amount of the acyclovir compound in the administration composition is an effective amount of acyclovir compound, which can be determined by those skilled in the art depending on the condition for which it is administered. The unit dosage form may comprise, for example, from about 0.01% to 10%, or about 0.01% to about 7%, or about 0.5% to about 4.0% of acyclovir compound. In alternative embodiments, an acyclovir compound is added until the administration composition is saturated with the acyclovir compound. In aqueous vehicles, this may correlate to a acyclovir compound concentration of about 5%. In semi-aqueous vehicles, such as isopropylmyristate, this may correlate to about 0.01% acyclovir compound concentration. In other vehicles, such as a PEG/Water vehicle, the acyclovir compound concentration is about 3% upon saturation of the administration composition.

The present invention provides, in addition to compositions as described above, a method for improving skin conditions. The method comprises applying the topical composition to an affected area. Herpes simplex, herpes zoster, can be treated or prevented by administering an effective amount of the composition or dosage unit form(s) of the present invention to the animal.

EXAMPLES

The following examples illustrate the invention without limitation. All parts are given by weight unless otherwise indicated. Acyclovir and Cicloferon® used in the study was obtained from Liomont S.A. de C.V. All excipients were commercially purchased. All delivery agents were synthesized at Emisphere Technologies, Inc. (Tarrytown, N.Y.).

Human cadaver skin was obtained from the N.Y. Firefighters Skin Bank at New York Presbyterian Hospital. It was delivered frozen at −70° C., and stored in a media of 80/10/10 balanced salt solution/calf serum/glycerol with the antimicrobials sodium oxacillin and gentamicin. The allograft skin was suitable for use in the treatment of burn victims.

Preparation of Human Cadaver Skin

A heat separation process was used to separate the epidermis from the dermis prior to skin permeation studies. The cadaver skin was first rapidly thawed in a water bath and rinsed in DI water. The skin was then placed in a beaker of DI water at 60-62° C. for 90-120 seconds. Manual separation of the epidermis from the dermis was then possible. Each layer was then floated in a tray of DI water, then removed on a clear silicone treated PET support film. Skin not used immediately was refrozen at −76° C. for later studies.

Equipment & Apparatus for Skin Permeation Rate Studies

Skin permeation studies were performed using two compartment diffusion cells. Two different types of cells were used, a horizontal Franz type cell, and a horizontal in line flow through cell. The Franz cells were magnetically stirred, jacketed and kept at 33° C. with a recirculating heater. The flow through cells had no provision for stirring, and were converted for non-flow use by means of luer fittings and valves. Temperature was maintained by placing the flow through cells and their holder in an oven at 33° C. Sampling was performed manually at intervals from 2-20 hours. Typical study duration was 2-3 days. A pH 7.4 phosphate buffer was used as the receptor, and it was completely exchanged at each sample point.

Skin Permeation/Content Experiments

The permeation cells were equilibrated at 33° C., and the skin mounted between the two halves of the cell. The epidermis, or epidermis & dermis were used depending on the analysis technique. The skin was allowed to equilibrate with the receptor buffer in the cells for 30-90 minutes prior to the study start. The acyclovir topical composition was placed in the cell donor chamber at the study start. At the conclusion of the study, the acyclovir donor was rinsed from the cell, and the cell disassembled. The epidermis (and/or dermis) was removed from the cell, rinsed again, then extracted and assayed for acyclovir content.

Drug Assay Methods

Collected samples from skin permeation/content studies were assayed for acyclovir and/or SNAC content by separate HPLC assay methods. Both methods were isocratic and used UV detection and conventional C8 and C18 columns. Specific details on each method can be found in Table 1 below:

TABLE 1

| | HPLC assay methods | |
|---|---|---|
| | Acyclovir | SNAC |
| column | Phenomenex #00G-0081-E0 IB-Sil C8, 5 micron 250 × 4.6 mm | Higgins Analytical #KS-0546-C185 5 micron 50 × 4.6 mm |
| ratio | A/B, 90/10 | A/B, 55/45 |
| Sol. A | 25 mM KH$_2$PO$_4$ (3.403 g/l) + ~150 µl 85% phosphoric acid to pH 2.75 | acetonitrile/water/acetic acid/1N HCl 100/891/4/5 |
| Sol. B flow rate | methanol isocratic 1.0 ml/min | acetonitrile/water/acetic acid/697/300.3 isocratic 1.0 ml/min |

Formulations Used in Skin Permeation Studies

Topical dosage forms prepared were in the form of polymer thickened gels and suspensions. The excipients, delivery agent compound, and thickener were typically prepared first by means of an impeller type mixer or homogenizer for two minutes. For non-Cicloferon-based formulations, the drug was added last, and blended for two minutes using a homogenizer, or manually with a positive displacement pipette. The addition order was reversed with Cicloferon based formulations. The following formulations were prepared:

TABLE 2

| Formulation | Ingredient | Amount (wt %) |
|---|---|---|
| A | hydroxypropylcellulose | 2.0 |
| | ethanol | 38.9 |
| | water | 49.9 |
| | triethanolamine | 0.5 |
| | SNAC (delivery agent) | 4.1 |
| | Acyclovir | 4.6 |
| B (control) | Cicloferon | 100 |
| C | Cicloferon | 95.0 |
| | SNAC | 5.0 |
| D | Cicloferon | 90.9 |
| | Pegylated SNAC | 9.1 |
| E | Cicloferon | 97.0 |
| | SNAC | 3.0 |
| F | Cicloferon | 74.2 |
| | Ethanol | 21.7 |
| | SNAC | 4.1 |
| G | Cicloferon | 67.3 |
| | Ethanol | 4.5 |
| | SNAC | 17.9 |
| | isopropylmyristate (IPM) | 10.2 |
| H | ethanol | 41.6 |
| | IPM | 40.8 |
| | water | 4.0 |
| | hydroxypropylcellulose | 2.0 |
| | ethylcellulose N22F | 9.4 |
| | Acylovir | 2.3 |
| I | hydroxypropylcellulose | 1.9 |
| | ethanol | 41.5 |
| | water | 52.2 |
| | triethanolamine | 0.5 |
| | SNAC | 7.2 |
| | IPM | 4.5 |
| | acyclovir | 3.8 |
| J | hydroxypropylcellulose | 2.1 |
| | ethanol | 41.5 |
| | water | 52.2 |
| | triethanolamine | 0.5 |
| | acyclovir | 3.7 |
| K | hydroxypropylcellulose | 0.6 |
| | ethanol | 11.2 |
| | water | 14.0 |
| | triethanolamine | 0.1 |
| | IPM | 71.1 |
| | acyclovir | 3.0 |
| L | hydroxypropylcellulose | 2.0 |
| | ethanol | 54.5 |
| | water | 34.8 |
| | triethanolamine | 0.5 |
| | SNAC | 4.0 |
| | acyclovir | 4.2 |

TABLE 2-continued

Formulations Tested in Acyclovir Permeation and Retention Studies

| Formulation | Ingredient | Amount (wt %) |
|---|---|---|
| M | hydroxypropylcellulose | 2.0 |
|   | ethanol | 23.3 |
|   | water | 66.0 |
|   | triethanolamine | 0.5 |
|   | SNAC | 4.0 |
|   | acyclovir | 4.2 |
| N | hydroxypropylcellulose | 2.0 |
|   | ethanol | 38.9 |
|   | water | 49.9 |
|   | triethanolamine | 0.5 |
|   | SNAC | 4.1 |
|   | acyclovir | 4.6 |

Acyclovir Skin Permeation and Dermal/Epidermal Content

Figure 2:
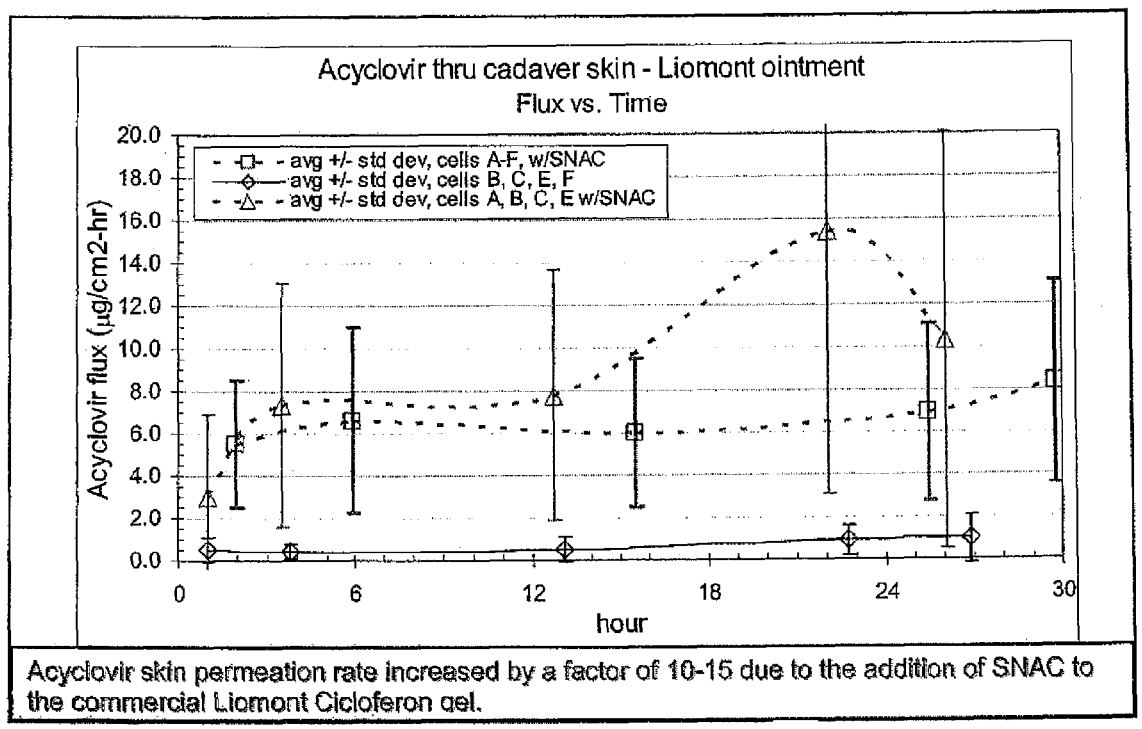
FIGS. 2-11 are graphs of acyclovir flux over time through cadaver skin.
Figure 3:
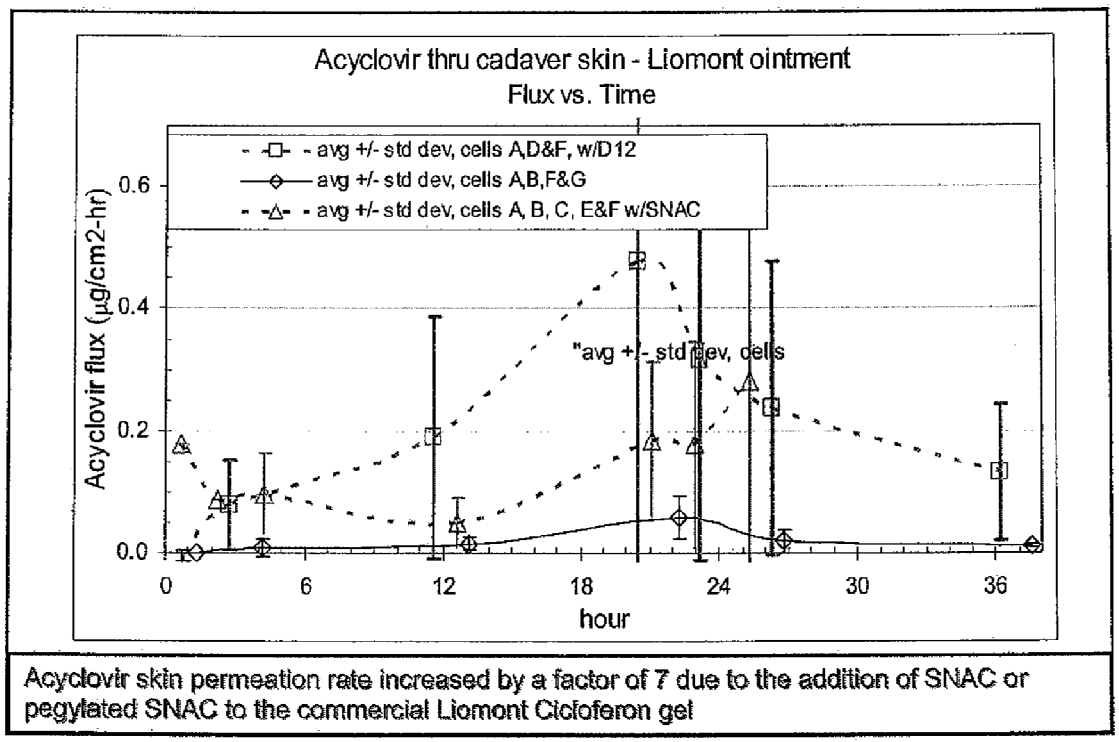
Figure 4:
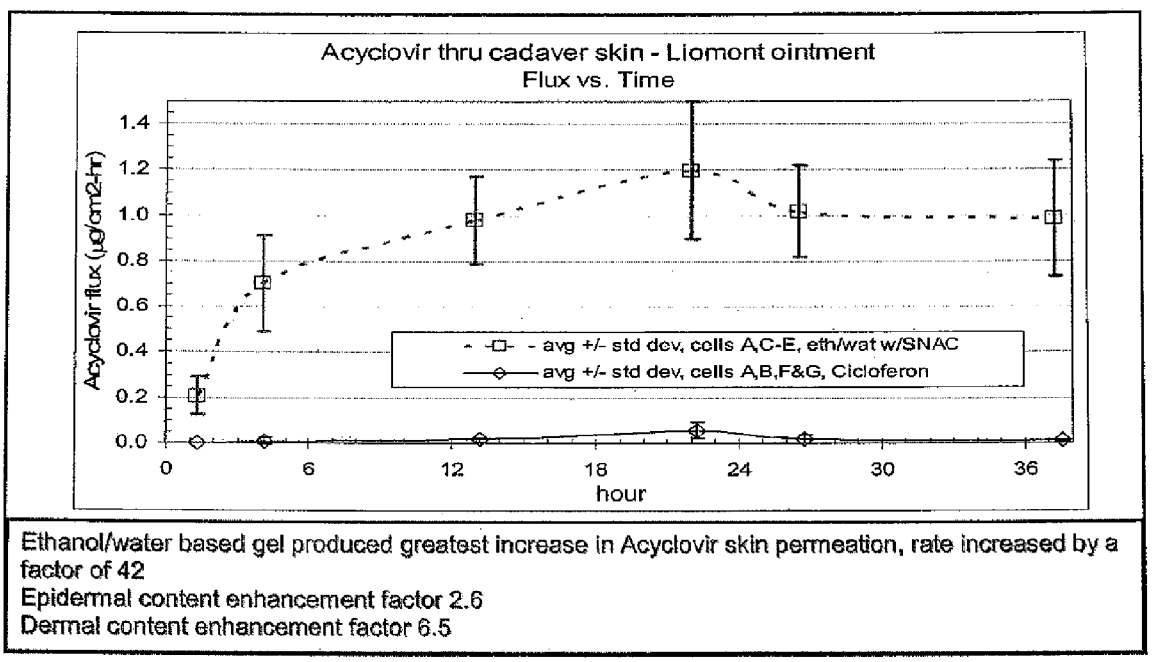
Figure 5:
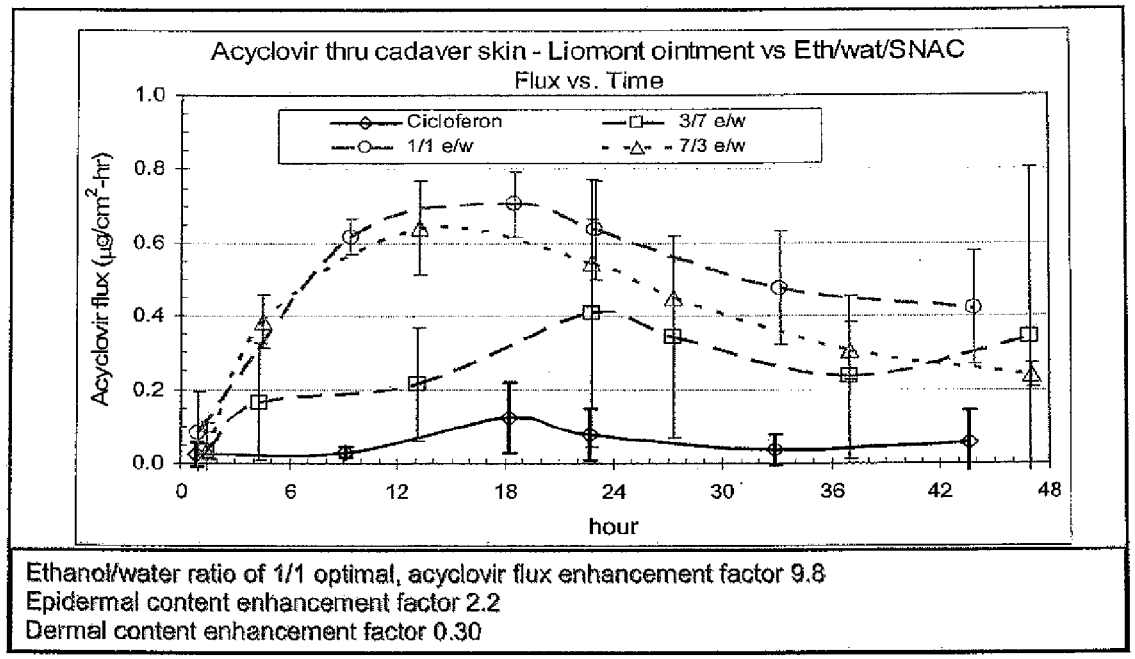
Figure 6:
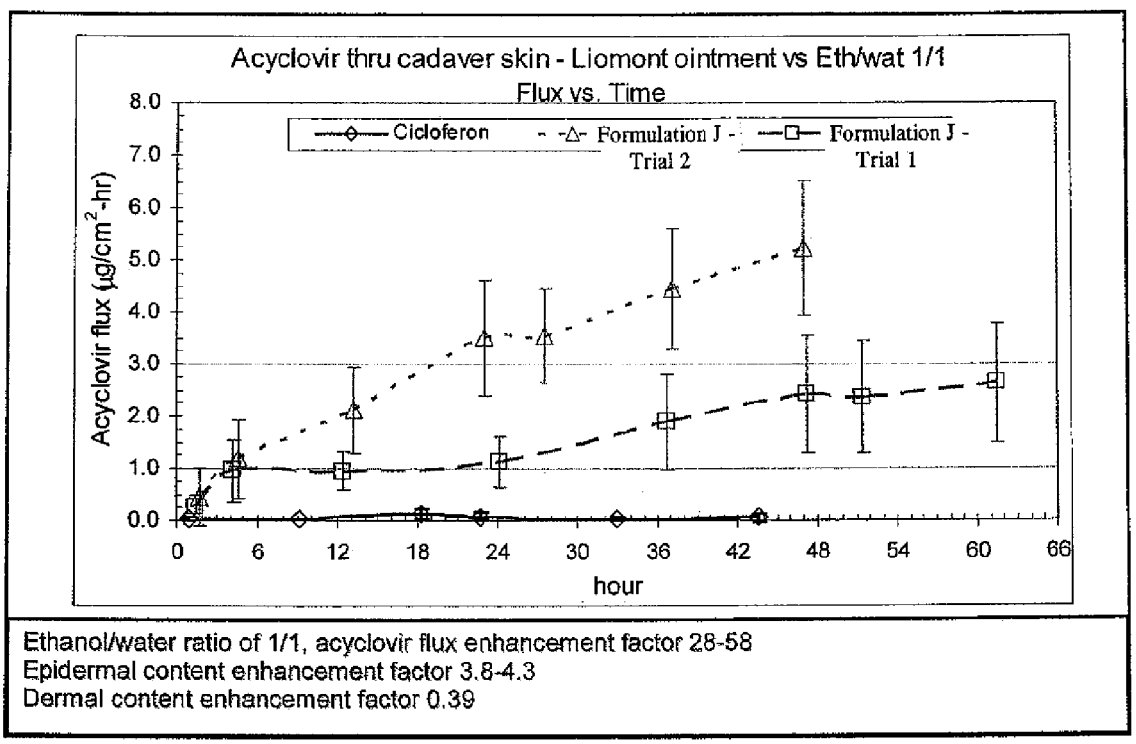
Figure 7:
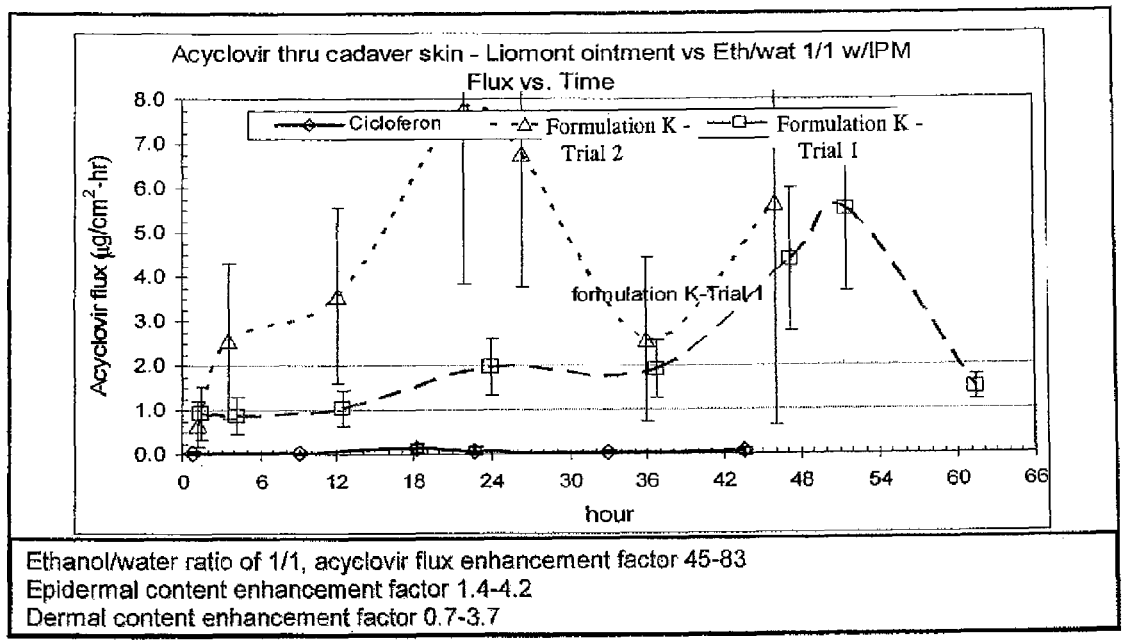
Figure 8:
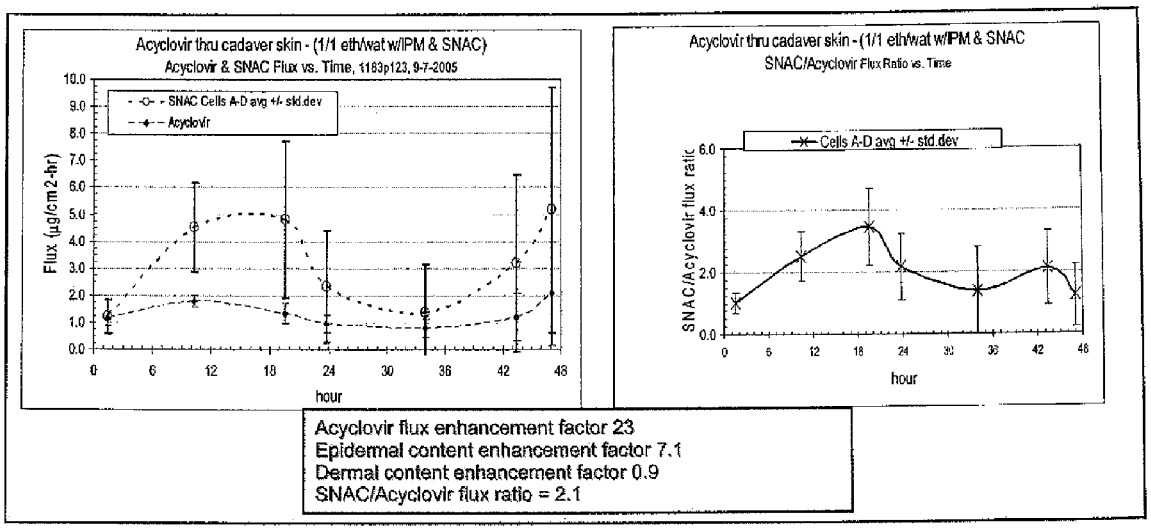
Figure 9:
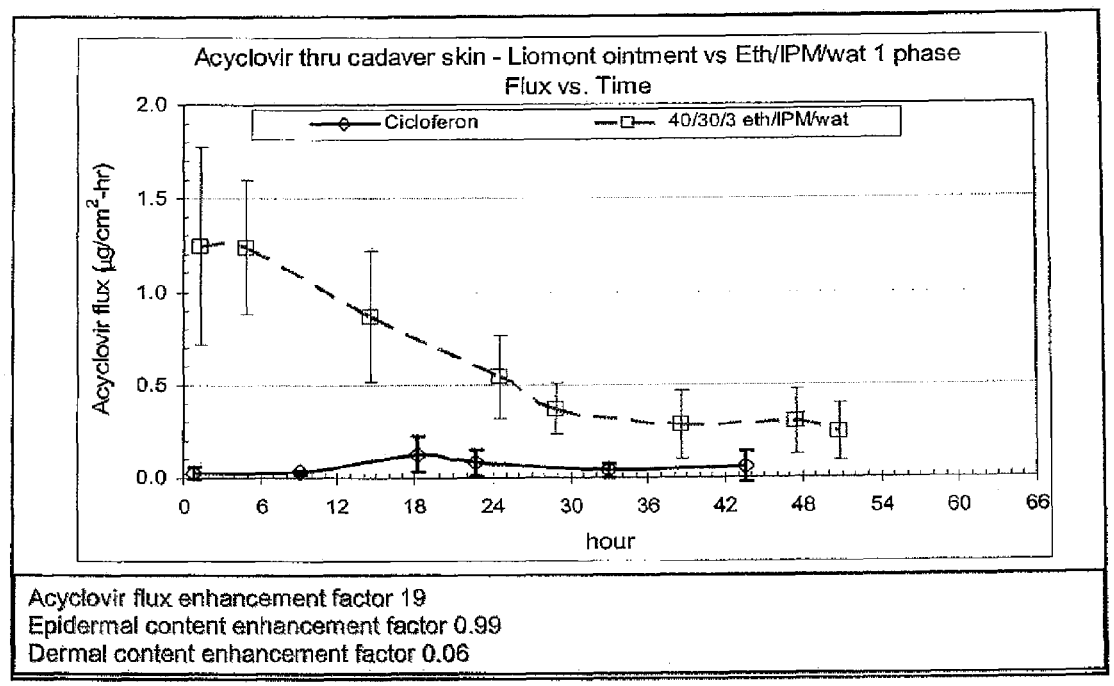
Figure 10:
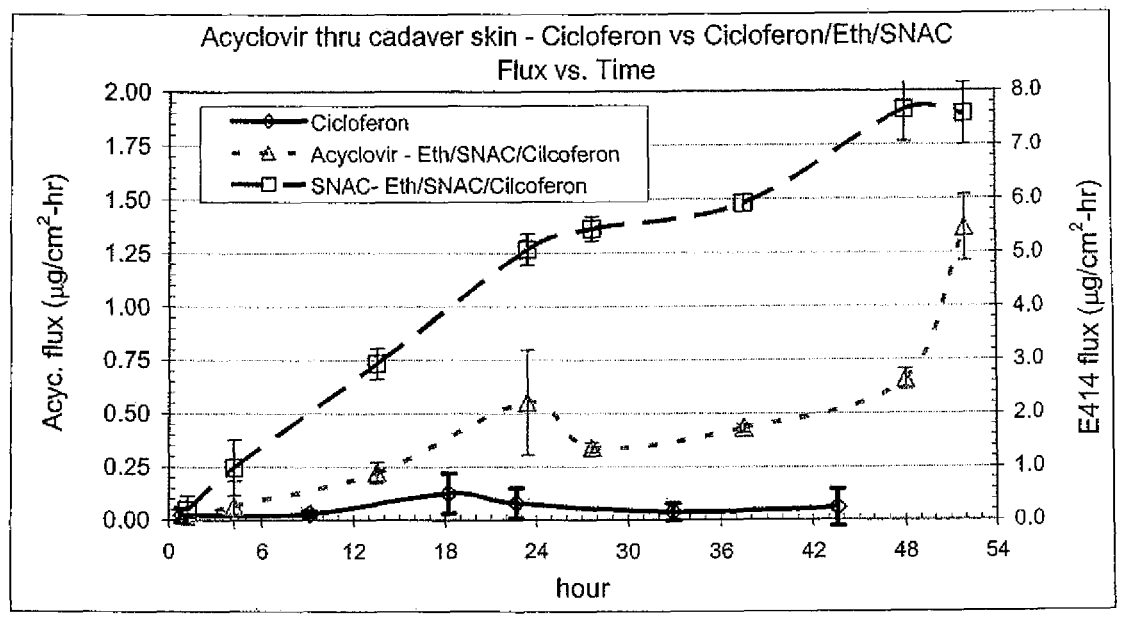
Figure 11:
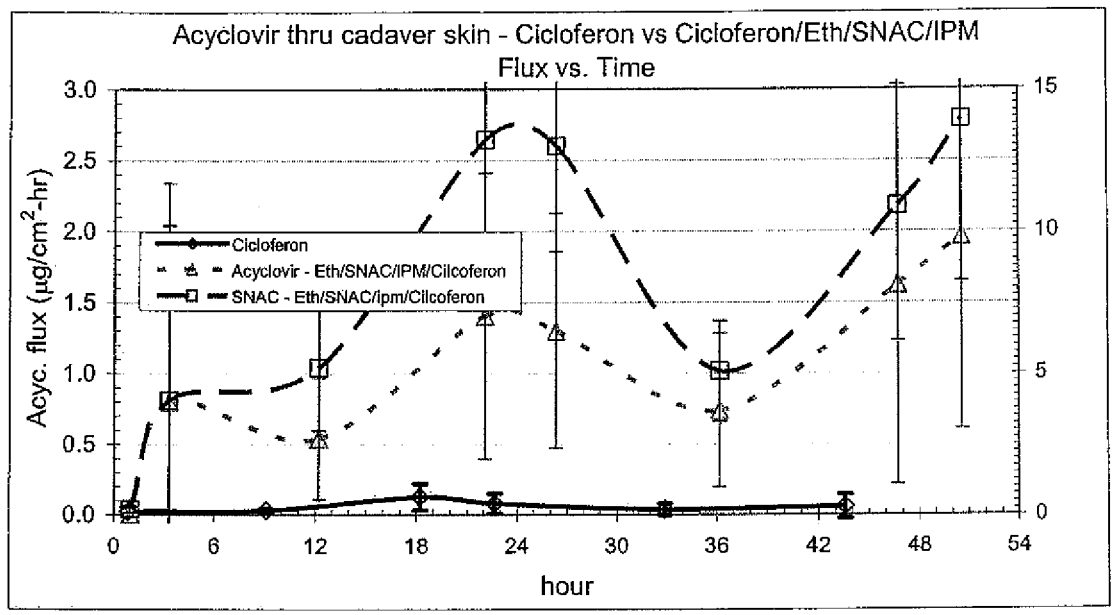

The performance of various formulation described below was measured via the acyclovir skin flux rate as compared to the control Cicloferon-only formulation (Formulation B). The epidermal acyclovir concentrations were also measured. These results are shown below in Tables 3 and 4:

FIGS. 2-4 show the acyclovir flux profiles over time for each formulation listed in table 2. The studies run in this group included a comparison of skin permeation across epidermis only, and epidermis+dermis (FIG. 2). Pegylated SNAC (MW approx. 601) was also evaluated as a delivery agent compound in these studies, results shown in FIG. 3. Results from a reformulated base of SNAC in an ethanol/water gel are shown in FIG. 4. An ethanol content of 50% or more appeared to produce the highest acyclovir flux in this example at a factor of 9.8× Cicloferon, as shown in FIG. 5.

Flow thru cells converted to non-flow thru use were setup for permeation studies in the radiolabeled lab. The cells were magnetically stirred, jacketed and kept at 33° C., and a pH 7.4 phosphate buffer was used as the receptor. These cells have a recessed surface for placement of the test membrane. Epidermis only was used in these cells for $^3$H acyclovir studies. The epidermis was placed over 20 mm diameter 0.45 μm nylon filter disks prior to mounting in the cell. The source of $^3$H acyclovir was Sigma (#A1562, lots 104K9602 & 026K9600) with a specific activity of 15 & 45 Ci/mmol respectively in a solution of 3/7 ethanol/water.

At the conclusion of the experiment, the epidermal membrane was removed and rinsed. Epidermal retention was determined for non-tritiated acyclovir by tissue extraction in a buffer/methanol solution followed by HPLC assay. For $^3$H-acyclovir the tissue was dissolved by Soluene 350/buffer

TABLE 3

Acyclovir skin permeation studies:

| Formulation | Analysis Technique | Amount Applied (μL/cm2) | # cells (n) | Acyclovir retention -- epidermis (μg/g) | Acyclovir retention -- dermis (μg/g) | Acyclovir flux through epidermis (μg/cm2 * hr)) | Skin Donor | Cells | Flux ratio (Compared to control of same donor) |
|---|---|---|---|---|---|---|---|---|---|
| A | A | 160 | 4 | 420 ± 180 | 130 ± 30 | 0.98 ± 0.23 | A | Crown | 42.61 |
| B | A | 105 | 4 | 160 ± 160 | 20 ± 30 | 0.023 ± 0.015 | A | in-line | NA |
| C | A | 210 | 5 | 9 ± 17 | 0.5 ± 0.6 | 0.15 ± 0.14 | A | in-line | 6.521 |
| D | A | 105 | 3 | <LD | 20 ± 30 | 0.2 ± 0.2 | A | in-line | 8.70 |
| E | A | 210 | 5 | 1030 ± 900 | 250 ± 90 | 8.8 ± 7.0 | B | in-line | 14.67 |
| E | B | 320 | 6 | — | — | 6.70 ± 3.80 | B | Crown | 11.17 |
| B | B | 320 | 4 | — | — | 0.60 ± 0.66 | B | Crown | NA |
| E | C | 37.5 | 6 | — | 630 ± 470 | NA | B | — | — |
| B | C | 37.5 | 6 | — | 1420 ± 730 | NA | B | — | — |

Analysis Technique A Acyclovir skin permeation followed by extgraction from skin layers, dermis + epidermis/stratum corneum.
Analysis Technique B epidermis/stratum corneum only.
Analysis Technique C direct donor application to dermis.

TABLE 4

Acyclovir skin permeation studies: ethanol/water based vehicle

| Formulation | Amount Applied (μL/cm2) | # cells (n) | Acyclovir retention -- epidermis (μg/g) | (Cv %) | Acyclovir retention -- dermis (μg/g) | (Cv %) | Acyclovir flux through epidermis (μg/cm2 * hr)) | (Cv %) | Cells | Flux ratio (Compared to control of same donor) |
|---|---|---|---|---|---|---|---|---|---|---|
| F | 120 | 6 | 135 ± 4 | 25.2 | 6 ± 2 | 33.3 | 0.68 ± 0.19 | 27.9 | Crown | 11.72 |
| G | 80 | 7 | 355 ± 80 | 22.5 | 257 ± 148 | 57.6 | 0.96 ± 0.72 | 75.0 | in-line | 16.55 |
| H | 120 | 6 | 208 ± 109 | 52.4 | 21 ± 23 | 109.5 | 1.12 ± 0.27 | 24.1 | in-line | 19.3 |
| I | 160 | 4 | 1490 ± 270 | 18.1 | 298 ± 296 | 99.3 | 1.36 ± 0.64 | 47.1 | in-line | 23.4 |
| J - Trial 1 | 160 | 4 | 796 ± 278 | 34.9 | 98 ± 30 | 30.6 | 1.62 ± 0.70 | 43.2 | Crown | 27.9 |
| K -- Trial 1 | 105 | 5 | 290 ± 221 | 76.2 | 222 ± 63 | 28.4 | 2.6 ± 0.8 | 30.8 | in-line | 44.8 |
| J - Trial 2 | 160 | 6 | 912 ± 136 | 14.90 | 102 ± 333 | 326.5 | 3.34 ± 0.95 | 28.4 | Crown | 57.6 |
| K -- Trial 2 | 105 | 5 | 891 ± 478 | 53.6 | 1248 ± 1266 | 101.4 | 4.8 ± 2.9 | 60.4 | in-line | 82.8 |
| L | 160 | 4 | 728 ± 909 | 124.9 | 188 ± 122 | 64.9 | 0.43 ± 0.09 | 20.9 | Crown | 7.41 |
| M | 105 | 5 | 356 ± 95 | 26.7 | 423 ± 457 | 108.0 | 0.28 ± 0.24 | 85.7 | in-line | 4.83 |
| N | 160 | 5 | 459 ± 198 | 43.1 | 131 ± 95 | 72.5 | 0.57 ± 0.10 | 17.5 | Crown | 9.83 |
| B (control) | 105 | 5 | 211 ± 401 | 190.0 | 334 ± 576 | 172.5 | 0.058 ± 0.055 | 94.8 | in-line | — |

All cells in Table 4 were analyzed via extraction Technique A followed by scintillation counting for calculation of epidermal retention. Beta counting of all samples was performed by diluting 0.5 ml of each sample with 1.0 ml of scintillation fluid (Perkin-Elmer Optiphase Hisafe II #1200-436). The extraction solvent for epidermal content was a 1:4 mixture of ph 7.4 buffer:tissue solubilizer (Perkin-Elmer Soluene 350 #600-3038).

$^3$H Acyclovir Skin Permeation

Two PEG-based formulations were prepared, both formulations also containing ~7.5% ethanol by volume. The first formulation contained about 5 wt % acyclovir (Formulation O) and the second formulation contained about 5 wt % acyclovir and about 5 wt % SNAC (Formulation P).

Results of the $^3$H acyclovir skin permeation trials are set forth below in Table 6:

TABLE 6

3H Acyclovir skin permeation studies with Cicloferon with and without SNAC

| Analysis Technique | Formulation | cells (n) | Acyclovir retention -- epidermis (μg/g) | Acyclovir retention -- dermis (μg/g) | (Cv %) | Acyclovir flux through epidermis (μg/cm2 * hr)) | (Cv %) | Skin Donor | Cells | Flux ratio (Compared to control of same donor) |
|---|---|---|---|---|---|---|---|---|---|---|
| B | O | 3 | 21 ± 4 | 19.0 | — | 0.046 ± 0.006 | 13.0 | C | in-line | — |
| B | P | 5 | 37 ± 14 | 37.8 | 1.76 | 0.098 ± 0.009 | 9.2 | C | in-line | 2.13 |
| B | O | 3 | 5 ± 2 | 40.0 | — | 0.011 ± 0.001 | 9.1 | D | in-line | — |
| B | P | 7 | 38 ± 37 | 102.7 | 7.6 | 0.011 ± 0.004 | 36.4 | D | in-line | 1.00 |

Figure 12:
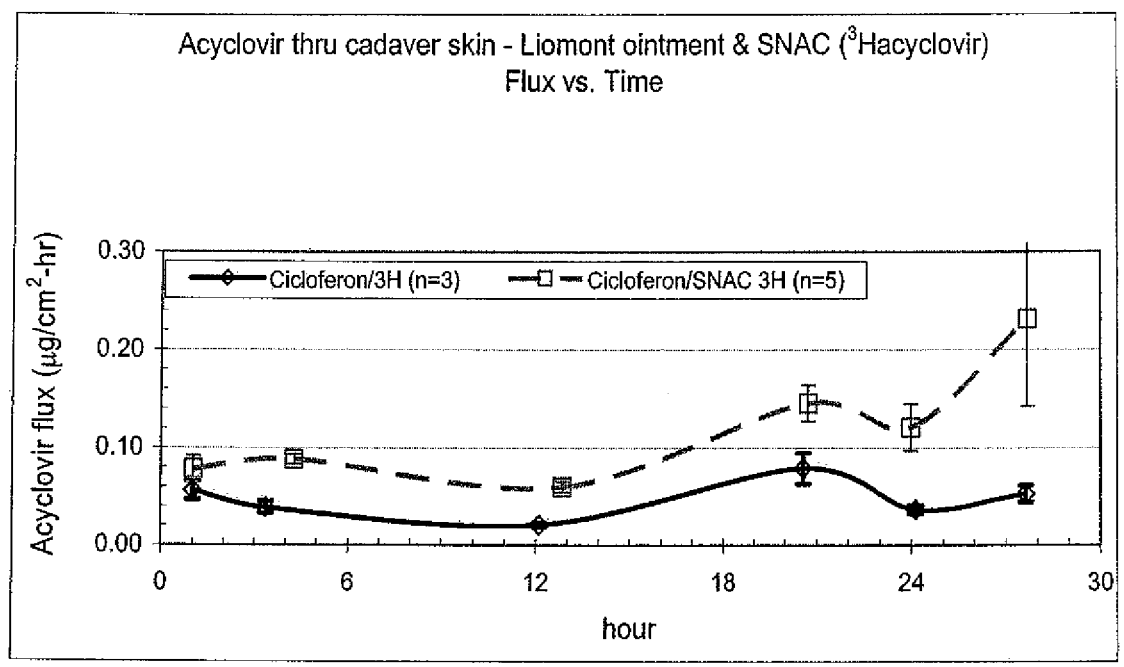
FIGS. 12 and 14 are graphs of $^3$H acyclovir flux over time through cadaver skin.
Figure 13:
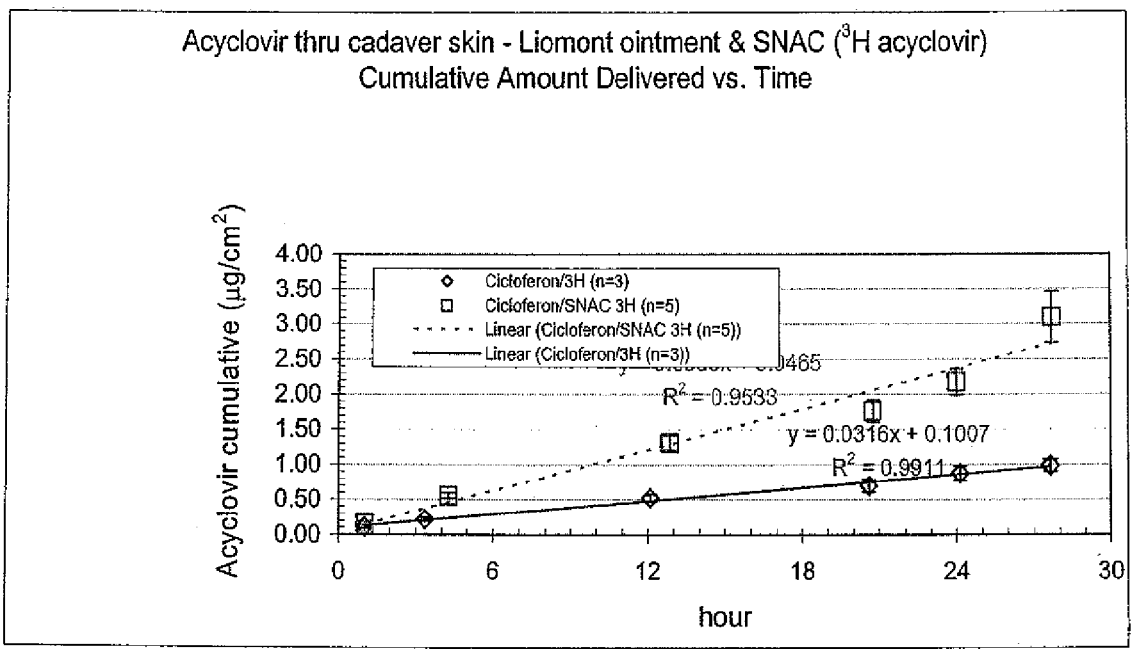
FIGS. 13 and 15 are linear regression models of FIGS. 12 and 14.
Figure 14:
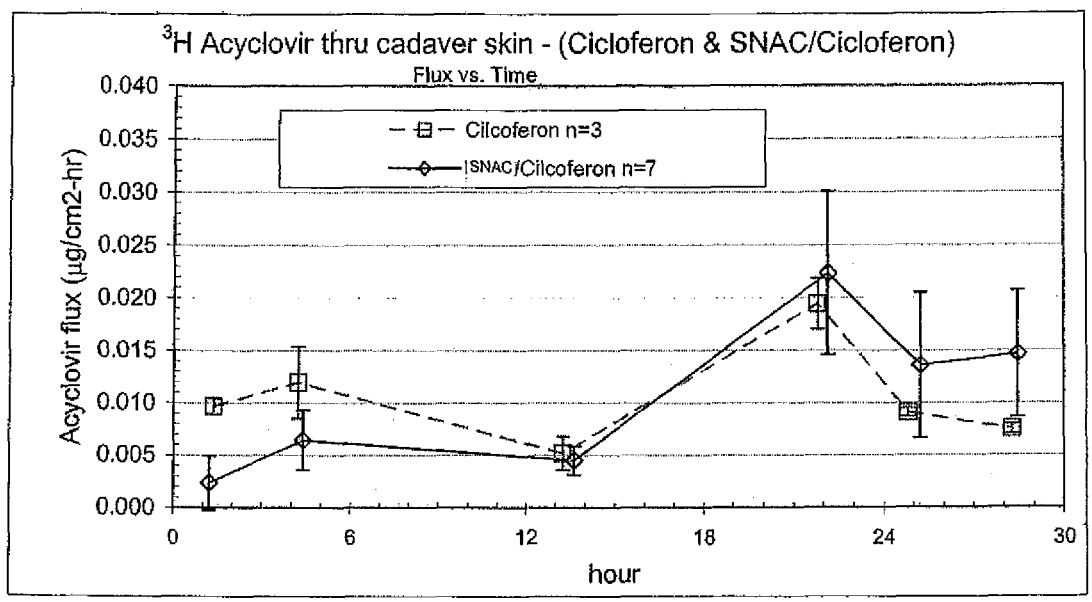
Figure 15:
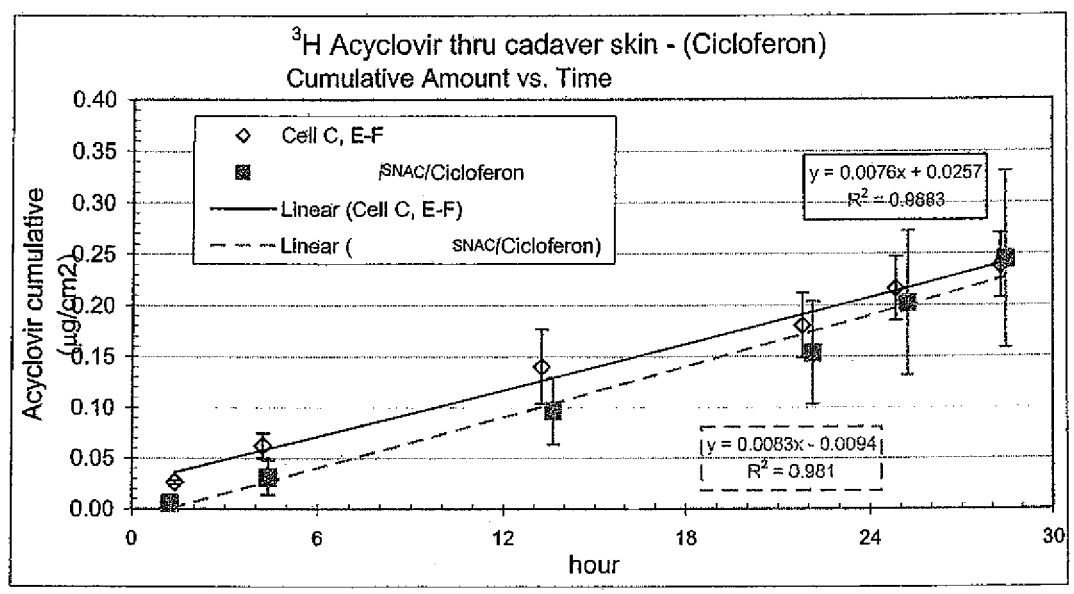

The acyclovir flux profiles for both formulations are shown in FIGS. 12 & 14. FIG. 13 shows the cumulative amount of acyclovir delivered. The slopes were calculated by linear regression.

Acyclovir skin permeation of the control (Cicloferon) across all four skin donors used in these studies is listed below in Table 7:

TABLE 7

Acyclovir retention and flux from control across all skin donors

| Analysis Technique | Formulation | # cells (n) | Acyclovir retention -- epidermis (μg/g) | Acyclovir retention -- dermis (μg/g) | Acyclovir flux through epidermis (μg/cm2 * hr)) | Skin Donor | Cells |
|---|---|---|---|---|---|---|---|
| A | B | 4 | 160 ± 160 | 20 ± 30 | 0.023 ± 0.015 | A | in-line |
| B | B | 4 | — | — | 0.60 ± 0.66 | B | Crown |
| A | B | 5 | 211 ± 401 | 334 ± 576 | 0.058 ± 0.055 | C | in-line |
| B | B ($^3$H) | 3 | 21 ± 4 | — | 0.046 ± 0.006 | C | in-line |
| B | B | 4 | 311 ± 383 | — | 0.017 ± 0.015 | D | in-line |
| B | B ($^3$H) | 3 | 5 ± 2 | — | 0.011 ± 0.001 | D | in-line | type A (Analysis Technique) Acyclovir skin permeation followed by extgraction from skin layers, dermis + epidermis/stratum corneum.
type B (Analysis Technique) epidermis/stratum corneum only.

The average values ranged from 0.011-0.60 μg/cm$^2$-hr. The last skin donor listed was used in several studies including $^3$H acyclovir formulations. The skin permeation result from the $^3$H acyclovir Cicloferon was 79% & 65% (two skin donors) of the value obtained using the non tritiated control and conventional HPLC sample assay.

What is claimed is:

1. A pharmaceutical composition comprising
   (a) about 1% to about 10% by weight of acyclovir or a salt thereof;
   (b) a vehicle for topical delivery comprising alcohol and water at a ratio of 1:1 to 7:3; and
   a delivery agent compound which is N-(8-[2-hydroxybenzoyl]amino)caprylic acid or a salt thereof;
   wherein the pharmaceutical composition is a topical pharmaceutical composition.

2. The pharmaceutical composition of claim 1, wherein the delivery agent compound is a sodium salt of N-(8-[2-hydroxybenzoyl]-amino)caprylic acid.

3. The pharmaceutical composition of claim 1, wherein the vehicle for topical delivery further comprises polyethylene glycol.

4. The pharmaceutical composition of claim 1, wherein the acyclovir or salt thereof component epidermal flux enhancement factor is 4 or higher.

5. The pharmaceutical composition of claim 1, further comprising one or more additional active agents selected from anti-allergic medications, glucocorticoids, corticosteroids, anti-inflammatory agents, pain relievers, local anesthetics, and combinations thereof.

6. The pharmaceutical composition of claim 5, where the one or more additional active agents is selected from oxatamide, betamethasone, valerate, dexamethasone, triamcinolone acetonide, clobetasone butyrate, hydrocortisone, triamcinolone, flurbiprofen, ketorolace, lidocaine, benzocaine, articaine, chlorprocaine, cocaine, dydloninem, proparacaine, mepivacaine, prilocalne, procaine, tetracaine, pramoxin, and combinations thereof.

7. The pharmaceutical composition of claim 1, wherein the alcohol is ethanol.

* * * * *